United States Patent
Kuchenbeiser et al.

(10) Patent No.: US 9,822,132 B2
(45) Date of Patent: Nov. 21, 2017

(54) HEXACOORDINATE SILICON-CONTAINING PRECURSORS FOR ALD/CVD SILICON-CONTAINING FILM APPLICATIONS

(71) Applicants: American Air Liquide, Inc., Fremont, CA (US); L'Air Liquide, Société Anonyme pour l'Etude et l'Exploitation des Procédés Georges Claude, Paris (FR)

(72) Inventors: Glenn Kuchenbeiser, Nnewark, DE (US); Christian Dussarrat, Tokyo (JP); Venkateswara R. Pallem, Hockessin, DE (US)

(73) Assignees: American Air Liquide, Inc., Fremont, CA (US); L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 14/905,859

(22) PCT Filed: Jul. 18, 2014

(86) PCT No.: PCT/US2014/047154
§ 371 (c)(1),
(2) Date: Jan. 18, 2016

(87) PCT Pub. No.: WO2015/009997
PCT Pub. Date: Jan. 22, 2015

(65) Prior Publication Data
US 2016/0152640 A1 Jun. 2, 2016

Related U.S. Application Data

(60) Provisional application No. 61/856,647, filed on Jul. 19, 2013.

(51) Int. Cl.
*C23C 16/00* (2006.01)
*C07F 7/02* (2006.01)
(Continued)

(52) U.S. Cl.
CPC ............... *C07F 7/025* (2013.01); *C07F 7/10* (2013.01); *C23C 16/345* (2013.01);
(Continued)

(58) Field of Classification Search
CPC ... C23C 16/345; C23C 16/401; C23C 16/455; C23C 16/45553; C07F 7/025; C07F 7/10
See application file for complete search history.

(56) References Cited

U.S. PATENT DOCUMENTS

| 2,590,039 A | 3/1952 | Richter et al. |
| 3,355,477 A | 11/1967 | Frye |

(Continued)

FOREIGN PATENT DOCUMENTS

| CN | 104341447 | 2/2015 |
| CN | 104447838 | 3/2015 |

(Continued)

OTHER PUBLICATIONS

Kost et al. Hydrazide-Based Hypercoordinate Silicon Compounds, 2004, Adv. in Organometallic Chem, 50, pp. 1-106.*
(Continued)

*Primary Examiner* — Kelly M Gambetta
(74) *Attorney, Agent, or Firm* — Patricia E. McQueeney

(57) ABSTRACT

Disclosed are hexacoordinate silicon-containing precursors, methods of synthesizing the same, and methods of using the same to deposit silicon-containing films using vapor deposition processes for manufacturing semiconductors, photovoltaics, LCD-TFT, flat panel type devices, refractory materials, or aeronautics. The hexacoordinate silicon-containing molecule have the following formula: (I), wherein each $L^1$, (Continued)

$L^2$, $L^3$ and $L^4$ is independently selected from oxygen or nitrogen atoms; $L^1$ and $L^2$ are joined together via a carbon bridge having one to three carbon atoms; $L^3$ and $L^4$ are joined together via a carbon bridge having one to three carbon atoms; $L^1$, $L^2$ and the carbon bridge forming a monoanionic ligand bonded to silicon; and $L^3$, $L^4$ and the carbon bridge form a monoanionic ligand bonded to silicon.

14 Claims, 1 Drawing Sheet

(51) Int. Cl.
*C07F 7/10* (2006.01)
*C23C 16/34* (2006.01)
*C23C 16/40* (2006.01)
*C23C 16/455* (2006.01)

(52) U.S. Cl.
CPC .......... *C23C 16/401* (2013.01); *C23C 16/455* (2013.01); *C23C 16/45553* (2013.01)

(56) References Cited

U.S. PATENT DOCUMENTS

| | | | |
|---|---|---|---|
| 4,841,084 | A | 6/1989 | Corriu et al. |
| 5,394,269 | A | 2/1995 | Takamatsu et al. |
| 6,391,803 | B1 | 5/2002 | Kim et al. |
| 6,465,387 | B1 | 10/2002 | Pinnavaia et al. |
| 6,736,993 | B1 | 5/2004 | Xu et al. |
| 6,869,638 | B2 | 3/2005 | Baum et al. |
| 7,125,582 | B2 | 10/2006 | McSwiney et al. |
| 7,192,626 | B2 | 3/2007 | Dussarrat et al. |
| 7,332,618 | B2 | 2/2008 | Meiere |
| 7,482,286 | B2 | 1/2009 | Misra et al. |
| 7,875,312 | B2 | 1/2011 | Thridandam et al. |
| 8,129,555 | B2 | 3/2012 | Cheng et al. |
| 8,828,505 | B2 | 9/2014 | Thridandam et al. |
| 2006/0045986 | A1 | 3/2006 | Hichberg et al. |
| 2006/0258173 | A1 | 11/2006 | Xiao et al. |
| 2007/0160774 | A1 | 7/2007 | Tsukada et al. |
| 2007/0275166 | A1 | 11/2007 | Thridandam et al. |
| 2009/0302434 | A1 | 12/2009 | Pallem et al. |
| 2010/0112211 | A1 | 5/2010 | Xu et al. |
| 2010/0164057 | A1 | 7/2010 | Hunks et al. |
| 2010/0317150 | A1 | 12/2010 | Hunks et al. |
| 2011/0045676 | A1 | 2/2011 | Park et al. |
| 2011/0061733 | A1 | 3/2011 | Hurley et al. |
| 2011/0250354 | A1 | 10/2011 | Pallem et al. |
| 2012/0277457 | A1 | 11/2012 | Lehmann et al. |
| 2013/0022745 | A1 | 1/2013 | Dussarrat et al. |
| 2013/0078392 | A1 | 3/2013 | Xiao et al. |
| 2014/0031502 | A1 | 1/2014 | Qin et al. |
| 2015/0087139 | A1 | 3/2015 | O'Neill et al. |

FOREIGN PATENT DOCUMENTS

| | | |
|---|---|---|
| EP | 1 310 500 | 5/2003 |
| EP | 1 563 117 | 2/2010 |
| EP | 2 154 141 | 2/2010 |
| EP | 2 392 691 | 12/2011 |
| EP | 2 444 405 | 4/2012 |
| JP | H06 132276 | 5/1994 |
| JP | H06 132284 | 5/1994 |
| JP | 2000 195801 | 7/2000 |
| JP | 2010 514918 | 5/2008 |
| KR | 2011 0009739 | 1/2011 |
| KR | 2012 0060843 | 6/2012 |
| KR | 10 2012 0078909 | 7/2012 |
| WO | WO 01 79578 | 10/2001 |
| WO | WO 2005 093126 | 10/2005 |
| WO | WO 2006 097525 | 9/2006 |
| WO | WO 2006 136584 | 12/2006 |
| WO | WO 2009 087609 | 7/2009 |
| WO | WO 2008 057616 | 5/2010 |
| WO | WO 2011 103282 | 8/2011 |
| WO | WO 2011 123792 | 10/2011 |
| WO | WO 2012 176988 | 12/2012 |
| WO | WO 2013 117326 | 11/2013 |
| WO | WO 2014 015232 | 1/2014 |
| WO | WO 2014 015237 | 1/2014 |

OTHER PUBLICATIONS

Xu et al. Synthesis and Characterization of Neutral cis-Hexacoordinate Bis(â-diketonate) Silicon(IV) Complexes, 2004, Inorg. Chem., 43, pp. 1568-1573.*
Chult et al. Reactivity of Penta- and Hexacoordinate Silicon Compounds and Their Role as Reaction Intermediates, 1993, Chem. Rev., 93, pp. 1371-1448.*
Baus, J.A. et al., "Neutral six-coordinate and cationic five-coordinate silicon(IV) complexes with two bidentate monoanionic N,S-pyridine-2-thiolato(--) ligands," Inorg. Chem, 2013, 52, 10664-10676.
Beckmann, J. et al., "The origin of ring strain and conformational flexibility in tri- and tetrasiloxane rings and their heavier Group 14 congeners," Organosilicon Chemistry VI: From Molecules to Materials, N. Auner and J. Weis, eds., 2005, Wiley-VCH Verlag GmbH, Weinheim, 252-258.
Dona, N. et al., "Novel dimeric pentacoordinate silicon complexes: unusual reactivity of electron-rich aminosilane intermediates," Organosilicon Chemistry VI: From Molecules to Materials, N. Auner and J. Weis, eds., 2005, Wiley-VCH Verlag GmbH, Weinheim, 271-278.
Dransfeld, A. et al., "The effect of silyl anion substituents on the stability and NMR characteristics of cyclic polyphosphines—an ab initio—NMR Study," Organosilicon Chemistry VI: From Molecules to Materials, N. Auner and J. Weis, eds., 2005, Wiley-VCH Verlag GmbH, Weinheim, 240-244.
Ebsworth, E.A.V. et al., "The preparation and properties of some silyl esters," J. Chem. Soc. (A), 1967, 69-72.
Eilingsfeld, H. et al., "Synthesen mit Amidchloriden, III. Synthese und Reaktionen von Chlorformamidiniumchloriden," Chemische Berichte vol. 97, Issue 5, May 1964, 1232-1245.
Von Frantzius, G. et al., "Strong evidence for an unconventional 1,2-(C->P)-silyl migration: DFT structures and bond strengths (compliance constants)," Organosilicon Chemistry VI: From Molecules to Materials, N. Auner and J. Weis, eds., 2005, Wiley-VCH Verlag GmbH, Weinheim, 211-215.
Gonzalez-Garcia et al., "Pentacoordinate mono(β-diketonato)- and hexacoordinate bis-(β-diketonato)-silicon(IV) complexes obtained from (thiocyanato-N)hydridosilanes," Polyhedron 41 (2012), 127-133.
Hassler, K. et al., "Preparations and x-ray structures of some silicon-phosphorus and silicon-arsenic cages," Organosilicon Chemistry VI: From Molecules to Materials, N. Auner and J. Weis, eds., 2005, Wiley-VCH Verlag GmbH, Weinheim, 228-232.
Herzog, U. et al., "Si NMR chemical shift tensors in organosilicon chalcogenides," Organosilicon Chemistry VI: From Molecules to Materials, N. Auner and J. Weis, eds., 2005, Wiley-VCH Verlag GmbH, Weinheim, 259-264.
Ionescu, E. et al., "Strong evidence for an unconventional 1,2-(C->P)-silyl migration: formation and reactions of a P-silyl phosphaalkene complex," Organosilicon Chemistry VI: From Molecules to Materials, N. Auner and J. Weis, eds., 2005, Wiley-VCH Verlag GmbH, Weinheim, 202-208.
Junold, K. et al., "Bis[N,N'-diisopropylbenzamidinato(-)]silicon(II): a silicon(II) compound with both a bidentate and a monodentate amidinato ligand," Angew. Chem. Int. Ed. 2012, 51, 7020-7023.
Junold, K. et al., "Novel neutral hexacoordinate benzamidinatosilicon(IV) complexes with $SiN_3OF_2$, $SiN_3OCl_2$, $SiN_3OBr_2$, $SiN_5O$ and $SiN_3O_3$ skeletons," Dalton Trans., 2011, 40, 9844-9857.
Lange, H. et al., "Hypersilyltelluro-substituted silanes and $(Ph_2SiTe)_3$," Organosilicon Chemistry VI: From Molecules to Materials, N. Auner and J. Weis, eds., 2005, Wiley-VCH Verlag GmbH, Weinheim, 265-270.

(56) References Cited

OTHER PUBLICATIONS

Karsch, H.H. et al., "Bis(amidinate) complexes of silicon and germanium," Eur. J. Inorg. Chem. 1998, 433-436.
Karsch, H.H. et al., "'Hypervalent' molecules—low valency candidates for materials?," Organosilicon Chemistry VI: From Molecules to Materials, N. Auner and J. Weis, eds., 2005, Wiley-VCH Verlag GmbH, Weinheim, 194-284.
Karsch, H.H. et al., "Silicon and germanium amidinates," Organosilicon Chemistry IV: From Molecules to Materials, N. Auner and J. Weis, eds., Wiley-VCH Verlag GmbH, Weinheim, Germany, 287-293.
Karsch, H.H. et al., "Silicon and germanium compounds with amidinate ligands," Organosilicon Chemistry V: From Molecules to Materials, N.. Auner and J. Weis, eds., 2003, Wiley-VCH Verlag GmbH, Weinheim, 270-276.
Kliem, S. et al., "Silyl group migrations between oxygen and nitrogen in aminosiloxanes," Organosilicon Chemistry VI: From Molecules to Materials, N. Auner and J. Weis, eds., 2005, Wiley-VCH Verlag GmbH, Weinheim, 216-221.
Mehring, M. et al., "Homo- and heterometallic bismuth silanolates," Organosilicon Chemistry VI: From Molecules to Materials, N. Auner and J. Weis, eds., 2005, Wiley-VCH Verlag GmbH, Weinheim, 233-239.
Negrebetsky, V.V. et al., "Dynamic stereochemistry of hypervalent silicon, germanium and tin compounds containing amidomethyl C,O-chelating ligands," Russian Chemical Bulleting, vol. 46, No. 11, Nov. 1997, 1807-1831.
Pietschnig, R. et al., "Terphenyl phosphanosilanes," Organosilicon Chemistry VI: From Molecules to Materials, N. Auner and J. Weis, eds., 2005, Wiley-VCH Verlag GmbH, Weinheim, 222-227.
Siddiqi, K.S. et al., "Group IV metal complexes of the dithiocarbamate ligand derived from propanediamine," Synthesis and Reactivity in Inorganic and Metal-Organic chemistry, 23:5, 685-693.
Veith, M. et al., "Silanols as precursors to cyclo- and polysiloxanes," Organosilicon Chemistry VI: From Molecules to Materials, N. Auner and J. Weis, eds., 2005, Wiley-VCH Verlag GmbH, Weinheim, 245-251.
Wagler, J. et al., "Unique switching of coordination number with imine and enamine complexes of Group 14 elements," Organosilicon Chemistry VI: From Molecules to Materials, N. Auner and J. Weis, eds., 2005, Wiley-VCH Verlag GmbH, Weinheim, 279-284.
Xu, C. et al., "Synthesis and characterization of neutral cis-hexacoordinate bis($\beta$-diketonate) silicon(IV) complexes," Inorganic Chemistry 2004, 43, 1568-1573.
International Search Report and Written Opinion for corresponding PCT/US2013/051255, dated Oct. 16, 2013.
International Search Report and Written Opinion for related PCT/US2013/051244, dated Oct. 16, 2013.
International Search Report and Written Opinion for related PCT/US2013/051249, dated Oct. 16, 2013.
International Search Report and Written Opinion for related PCT/US2013/051264, dated Oct. 16, 2013.
International Search Report and Written Opinion for corresponding PCT/US2014/047154, dated Sep. 29, 2014.
Asay,M. et al., "N-heterocyclic carbene analogues with low-valent Group 13 and Group 14 elements: syntheses, structures, and reactivities of a new generation of multitalented ligands," Chem. Rev. 2011, 111, 354-396.
Herrmann, W.A. et al., "N-heterocyclic carbenes," Angew. Chem. Int. Ed. Engl. 1997, 36, 2162-2187.
Mattson, A.E. et al., "Thiazolium-catalyzed additions of acylsilanes: a general strategy for acyl anion addition reactions," J. Org. Chem. 2006, 71, 5715-5724.
Mück, F.M. et al., "Donor-stabilized silylenes with guanidinato ligands," Eur. J. Inorg. Chem. 2013, 5821-5825.
Naghammahmoodaljamali, "Review in cyclic compounds with heteroatom," Int. J. Curr. Res. Chem. Pharma. Sci. 1(9) (2014) 88-20.
Weidenbruch, M., "A stable silylenoid and a donor-stabilized chlorosilylene: low-coordinate silicon compounds—a never-ending story?," Angew. Chem. Int. Ed. 2006, 45, 4241-4242.
International Search Report and Written Opinion for related PCT/US2015/065077, dated Aug. 10, 2016.

\* cited by examiner

HEXACOORDINATE SILICON-CONTAINING PRECURSORS FOR ALD/CVD SILICON-CONTAINING FILM APPLICATIONS

CROSS-REFERENCE TO RELATED APPLICATIONS

This application is a 371 of International PCT Application PCT/US2014/047154, filed Jul. 18, 2014, which claims priority to U.S. provisional application No. 61/856,647, filed Jul. 19, 2013, the entire contents of which are incorporated herein by reference.

TECHNICAL FIELD

Disclosed are hexacoordinate silicon-containing precursors, methods of synthesizing the same, and methods of using the same to deposit silicon-containing films using vapor deposition processes for manufacturing semiconductor, photovoltaic, LCD-TFT, flat panel type devices, refractory materials, or aeronautics.

BACKGROUND

Si-containing thin films are used widely in the semiconductor, photovoltaic, LCD-TFT, flat panel type devices, refractory materials, or aeronautics industries. Si-containing thin films may be used for example, as dielectric materials having electrical properties which may be insulating ($SiO_2$, SiN, SiCN, SiCOH, MSiOx). Si-containing thin films may be used as conducting films, such as metal silicides or metal silicon nitrides. Due to the strict requirements imposed by downscaling of electrical device architectures towards the nanoscale (especially below 28 nm node), increasingly fine-tuned molecular precursors are required which meet the requirements of volatility (for ALD process), lower process temperatures, reactivity with various oxidants and low film contamination, in addition to high deposition rates, conformality and consistency of films produced.

Dussarrat et al. disclose a class of Si precursors for CVD of Si-containing films having the general formula $(R^1R^2N)_x SiH_{4-x}$ wherein x is between 1 and 4 and the R substituents are independently H, C1-C6 linear, branched, or cyclic carbon chains (WO2006/097525).

Hunks et al. disclose a wide range of Si-containing precursors in US2010/0164057, including silicon compounds having the formula $R_{4-x}SiL_x$, wherein x is an integer having a value from 1 to 3; R may be selected from H, branched and unbranched C1-C6 alkyl, C3-C8 cycloalkyl, and C6-C13 aryl groups; and L may be selected from isocyanato, methylethylketoxime, trifluoroacetate, triflate, acyloxy, β-diketiminate, β-di-iminate, amidinate, guanidinate, alkylamino, hydride, alkoxide, or format ligands. Pinnavaia et al. claim a method for the preparation of a porous synthetic, semi-crystalline hybrid organic-inorganic silicon oxide composition from silicon acetylacetonate and silicon 1,3-diketonate precursors (U.S. Pat. No. 6,465,387).

Hexacoordinate silicon containing compounds are also known in the art and have been proposed for CVD applications (see, e.g., Karsch and Segmüller, Silicon and Germanium Compounds with Amidinate Ligands, Organosilicon Chemistry V From Molecules to Materials pp. 271-276 of Organosilicon Chemistry V: From Molecules to Materials, WILEY-VCH Verlag GmbH & Co., 2003).

Despite the wide range of choices available for the deposition of Si containing films, additional precursors are continuously sought to provide device engineers the ability to tune manufacturing process requirements and achieve films with desirable electrical and physical properties.

NOTATION AND NOMENCLATURE

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "aryl" refers to aromatic ring compounds where one hydrogen atom has been removed from the ring. As used herein, the term "heterocycle" refers to a cyclic compound that has atoms of at least two different elements as members of its ring.

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "ph" refers to a phenyl group; the abbreviation "Am" refers to any amyl group (iso-amyl, sec-amyl, tert-amyl); the abbreviation "Cy" refers to a cyclic alkyl group (cyclobutyl, cyclopentyl, cyclohexyl, etc.); and the abbreviation "$N^Z$-amd" refers to $ZNC(CH_3)=NZ$, wherein Z is a defined alkyl group such as iPr or tBu.

As used herein, the acronym "SRO" stands for a Strontium Ruthenium Oxide film; the acronym "HCDS" stands for hexachlorodisilane; and the acronym "PODS" stands for pentachlorodisilane.

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

SUMMARY

Figure 1:
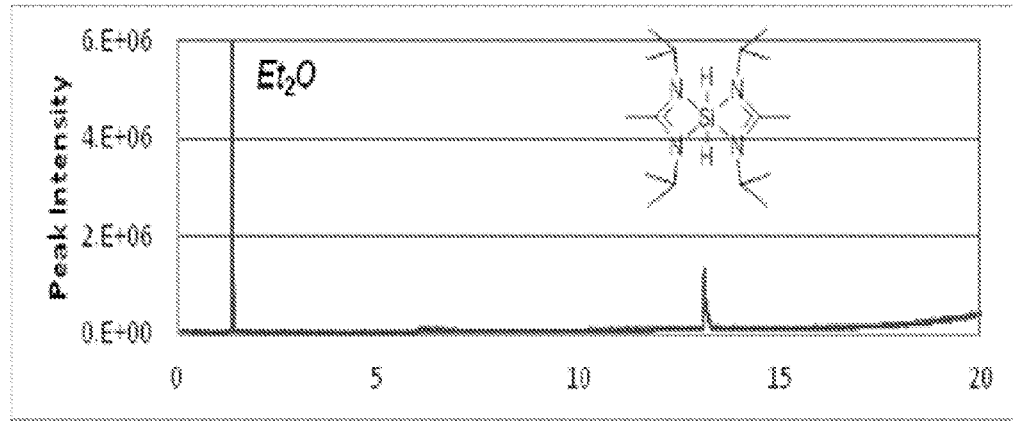
FIG. 1 is a gas chromatogram of the synthesis product of Example 1.

Disclosed are molecules having the following formula:

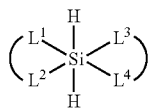

wherein each $L^1$, $L^2$, $L^3$ and $L^4$ is independently chosen from oxygen or nitrogen atoms; $L^1$ and $L^2$ being joined together via a carbon bridge having one to three carbon atoms; and $L^1$, $L^2$ and the carbon bridge forming a monoanionic ligand bonded to silicon. Similarly, $L^3$ and $L^4$ are joined together via a carbon bridge having one to three carbon atoms and $L^3$, $L^4$ and the carbon bridge form a monoanionic ligand bonded to silicon. The disclosed molecules may have one or more of the following aspects:

$L^1$, $L^2$, $L^3$ and $L^4$ each being a nitrogen atom;
the molecule having the following formula:

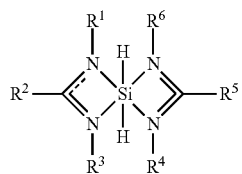

wherein $R^1$, $R^2$, $R^3$, $R^4$, $R^5$ and $R^6$ may each independently be H, a C1 to C6 alkyl group, or a C3-C20 aryl or heterocycle group;
$R^1$ and $R^2$ joined to form cyclic chains;
$R^2$ and $R^3$ joined to form cyclic chains;
$R^4$ and $R^5$ joined to form cyclic chains;
$R^5$ and $R^6$ joined to form cyclic chains;
$R^1$ and $R^2$ not joined to form cyclic chains;
$R^2$ and $R^3$ not joined to form cyclic chains;
$R^4$ and $R^5$ not joined to form cyclic chains;
$R^5$ and $R^6$ not joined to form cyclic chains;
$R^1$ being Me, Et, Pr, or Bu;
$R^2$ being H, Me, Et, Pr, or Bu;
$R^2$ being H;
$R^2$ being Me;
$R^3$ being Me, Et, Pr, or Bu;
$R^4$ being Me, Et, Pr, or Bu;
$R^5$ being H, Me, Et, Pr, or Bu;
$R^5$ being H;
$R^5$ being Me;
$R^6$ being Me, Et, Pr, or Bu;
the molecule having the following formula:

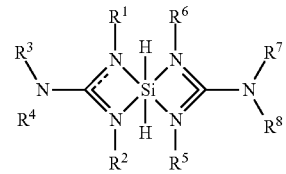

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group;
$R^1$ and $R^3$ joined to form cyclic chains;
$R^3$ and $R^4$ joined to form cyclic chains;
$R^2$ and $R^4$ joined to form cyclic chains;
$R^6$ and $R^7$ joined to form cyclic chains;
$R^7$ and $R^8$ joined to form cyclic chains;
$R^5$ and $R^8$ joined to form cyclic chains;
$R^1$ and $R^3$ not joined to form cyclic chains;
$R^3$ and $R^4$ not joined to form cyclic chains;
$R^2$ and $R^4$ not joined to form cyclic chains;
$R^6$ and $R^7$ not joined to form cyclic chains;
$R^7$ and $R^8$ not joined to form cyclic chains;
$R^5$ and $R^8$ not joined to form cyclic chains;
$R^1$ being Me, Et, Pr, or Bu;
$R^2$ being Me, Et, Pr, or Bu;
$R^3$ being H, Me or Et;
$R^3$ being Me or Et;
$R^4$ being H, Me or Et;
$R^4$ being Me or Et;
$R^5$ being Me, Et, Pr, or Bu;
$R^6$ being Me, Et, Pr, or Bu;
$R^7$ being H, Me or Et;
$R^7$ being Me or Et;
$R^8$ being H, Me or Et;
$R^8$ being Me or Et;
the molecule having the following formula:

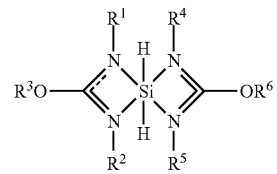

wherein $R^1$, $R^2$, $R^3$, $R^4$, $R^5$, and $R^6$ may each independently be H, a C1 to C6 alkyl group, or a C3-C20 aryl or heterocycle group;
$R^1$ and $R^3$ joined to form cyclic chains;
$R^2$ and $R^3$ joined to form cyclic chains;
$R^4$ and $R^6$ joined to form cyclic chains;
$R^5$ and $R^6$ joined to form cyclic chains;
$R^1$ and $R^3$ not joined to form cyclic chains;
$R^2$ and $R^3$ not joined to form cyclic chains;
$R^4$ and $R^6$ not joined to form cyclic chains;
$R^5$ and $R^6$ not joined to form cyclic chains;
$R^1$ being Me, Et, Pr, or Bu;
$R^2$ being Me, Et, Pr, or Bu;
$R^3$ being Me, Et, Pr, or Bu;
$R^4$ being Me, Et, Pr, or Bu;

R⁵ being Me, Et, Pr, or Bu;
R⁶ being Me, Et, Pr, or Bu;
the molecule having the following formula:

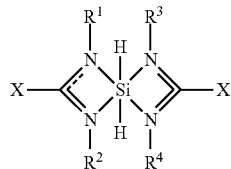

wherein R¹, R², R³, and R⁴ may each independently be H, a C1 to C6 alkyl group, or a C3-C20 aryl or heterocycle group, and each X may independently be Cl, Br, I, or F;
R¹ being Me, Et, Pr, or Bu;
R² being Me, Et, Pr, or Bu;
R³ being Me, Et, Pr, or Bu;
R⁴ being Me, Et, Pr, or Bu;
the molecule having the following formula:

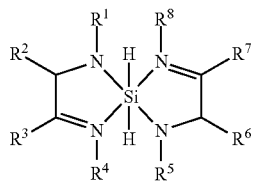

wherein R¹, R², R³, R⁴, R⁵, R⁶, R⁷ and R⁸ may each independently be H, a C1 to C6 alkyl group, or a C3-C20 aryl or heterocycle group;
R¹ and R² joined to form cyclic chains;
R² and R³ joined to form cyclic chains;
R³ and R⁴ joined to form cyclic chains;
R⁵ and R⁶ joined to form cyclic chains;
R⁶ and R⁷ joined to form cyclic chains;
R⁷ and R⁸ joined to form cyclic chains;
R¹ and R² not joined to form cyclic chains;
R² and R³ not joined to form cyclic chains;
R³ and R⁴ not joined to form cyclic chains;
R⁵ and R⁶ not joined to form cyclic chains;
R⁶ and R⁷ not joined to form cyclic chains;
R⁷ and R⁸ not joined to form cyclic chains;
R¹ being Me, Et, Pr, or Bu;
R² being H, Me, Et, or Pr;
R³ being H, Me, Et, or Pr;
R⁴ being Me, Et, Pr, or Bu;
R⁵ being Me, Et, Pr, or Bu;
R⁶ being H, Me, Et, or Pr;
R⁷ being H, Me, Et, or Pr;
R⁸ being Me, Et, Pr, or Bu;
the molecule having the following formula:

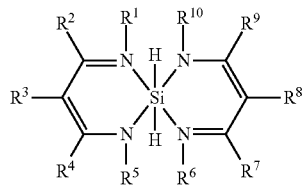

wherein R¹, R², R³, R⁴, R⁵, R⁶, R⁷, R⁸, R⁹, and R¹⁰ may each independently be H, a C1 to C6 alkyl group, or a C3-C20 aryl or heterocycle group;
R¹ and R² joined to form cyclic chains;
R² and R³ joined to form cyclic chains;
R³ and R⁴ joined to form cyclic chains;
R⁴ and R⁵ joined to form cyclic chains;
R⁶ and R⁷ joined to form cyclic chains;
R⁷ and R⁸ joined to form cyclic chains;
R⁸ and R⁹ joined to form cyclic chains;
R⁹ and R¹⁰ joined to form cyclic chains;
R¹ and R² not joined to form cyclic chains;
R² and R³ not joined to form cyclic chains;
R³ and R⁴ not joined to form cyclic chains;
R⁴ and R⁵ not joined to form cyclic chains;
R⁶ and R⁷ not joined to form cyclic chains;
R⁷ and R⁸ not joined to form cyclic chains;
R⁸ and R⁹ not joined to form cyclic chains;
R⁹ and R¹⁰ not joined to form cyclic chains;
R¹ being Me, Et, Pr, or Bu;
R² being Me, Et, Pr, or Bu;
R³ being H, Me, Et, or Pr;
R⁴ being Me, Et, Pr, or Bu;
R⁵ being Me, Et, Pr, or Bu;
R⁶ being Me, Et, Pr, or Bu;
R⁷ being Me, Et, Pr, or Bu;
R⁸ being H, Me, Et, or Pr;
R⁹ being Me, Et, Pr, or Bu;
R¹⁰ being Me, Et, Pr, or Bu;
L¹, L², L³ and L⁴ each being an oxygen atom;
the molecule having the following formula:

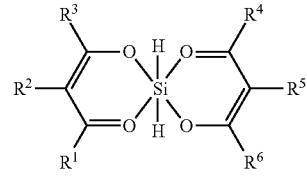

wherein R¹, R², R³, R⁴, R⁵, and R⁶ may each independently be H, a C1 to C6 alkyl group, or a C3-C20 aryl or heterocycle group;
R¹ and R² joined to form cyclic chains;
R² and R³ joined to form cyclic chains;
R⁴ and R⁵ joined to form cyclic chains;
R⁵ and R⁶ joined to form cyclic chains;
R¹ and R² not joined to form cyclic chains;
R² and R³ not joined to form cyclic chains;
R⁴ and R⁵ not joined to form cyclic chains;
R⁵ and R⁶ not joined to form cyclic chains;
R¹ being Me, Et, Pr, or Bu;
R² being H, Me, Et, or Pr;
R³ being Me, Et, Pr, or Bu;
R⁴ being Me, Et, Pr, or Bu;
R⁵ being H, Me, Et, or Pr;
R⁶ being Me, Et, Pr, or Bu;
the molecule having the following formula:

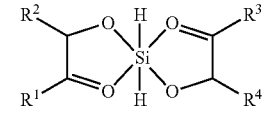

wherein $R^1$, $R^2$, $R^3$ and $R^4$ may each independently be H, a C1 to C6 alkyl group, or a C3-C20 aryl or heterocycle group;

$R^1$ and $R^2$ joined to form a cyclic chain;

$R^3$ and $R^4$ joined to form a cyclic chain;

$R^1$ and $R^2$ not joined to form a cyclic chain;

$R^3$ and $R^4$ not joined to form a cyclic chain;

$R^1$ being H, Me, Et, or Pr;

$R^2$ being H, Me, Et, or Pr;

$R^3$ being H, Me, Et, or Pr;

$R^4$ being H, Me, Et, or Pr;

the molecule having the following formula:

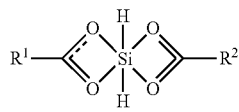

wherein $R^1$ and $R^2$ may be H, a C1 to C6 alkyl group, or a C3-C20 aryl or heterocycle group;

$R^1$ being H, Me, Et, Pr, or Bu;

$R^2$ being H, Me, Et, Pr, or Bu;

$L^1$ and $L^4$ being a nitrogen atom and $L^2$ and $L^3$ being an oxygen atom;

the molecule having the following formula:

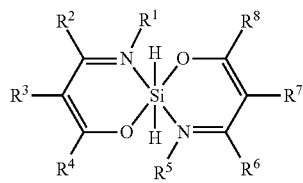

wherein $R^1$, $R^2$, $R^3$, $R^4$, $R^5$, $R^6$, $R^7$, and $R^8$ may each independently be H, a C1 to C6 alkyl group, or a C3-C20 aryl or heterocycle group;

$R^1$ and $R^2$ joined to form cyclic chains;

$R^2$ and $R^3$ joined to form cyclic chains;

$R^3$ and $R^4$ joined to form cyclic chains;

$R^5$ and $R^6$ joined to form cyclic chains;

$R^6$ and $R^7$ joined to form cyclic chains;

$R^7$ and $R^8$ joined to form cyclic chains;

$R^1$ and $R^2$ not joined to form cyclic chains;

$R^2$ and $R^3$ not joined to form cyclic chains;

$R^3$ and $R^4$ not joined to form cyclic chains;

$R^5$ and $R^6$ not joined to form cyclic chains;

$R^6$ and $R^7$ not joined to form cyclic chains;

$R^7$ and $R^8$ not joined to form cyclic chains;

$R^1$ being Me, Et, Pr, or Bu;

$R^2$ being H, Me, Et, Pr, or Bu;

$R^3$ being H, Me, Et, or Pr;

$R^4$ being H, Me, Et, Pr, or Bu;

$R^5$ being Me, Et, Pr, or Bu;

$R^6$ being H, Me, Et, Pr, or Bu;

$R^7$ being H, Me, Et, or Pr;

$R^8$ being H, Me, Et, Pr, or Bu;

the molecule having the following formula:

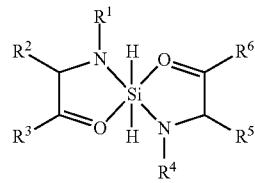

wherein $R^1$, $R^2$, $R^3$, $R^4$, $R^5$ and $R^6$ may each independently be H, a C1 to C6 alkyl group, or a C3-C20 aryl or heterocycle group;

$R^1$ and $R^2$ joined to form cyclic chains;

$R^2$ and $R^3$ joined to form cyclic chains;

$R^4$ and $R^5$ joined to form cyclic chains;

$R^5$ and $R^6$ joined to form cyclic chains;

$R^1$ and $R^2$ not joined to form cyclic chains;

$R^2$ and $R^3$ not joined to form cyclic chains;

$R^4$ and $R^5$ not joined to form cyclic chains;

$R^5$ and $R^6$ not joined to form cyclic chains;

$R^1$ being Me, Et, Pr, or Bu;

$R^2$ being H, Me, Et, or Pr;

$R^3$ being H, Me, Et, or Pr;

$R^4$ being Me, Et, Pr, or Bu;

$R^5$ being H, Me, Et, or Pr;

$R^6$ being H, Me, Et, or Pr;

the molecule having the following formula:

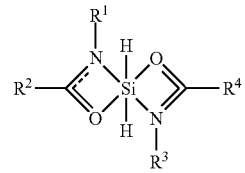

wherein $R^1$, $R^2$, $R^3$ and $R^4$ may each independently be H, a C1 to C6 alkyl group, or a C3-C20 aryl or heterocycle group;

$R^1$ and $R^2$ joined to form cyclic chains;

$R^3$ and $R^4$ joined to form cyclic chains;

$R^1$ and $R^2$ not joined to form cyclic chains;

$R^3$ and $R^4$ not joined to form cyclic chains; and $R^1$ being Me, Et, Pr, or Bu;

$R^2$ being H, Me, Et, Pr, or Bu;

$R^3$ being Me, Et, Pr, or Bu; and $R^4$ being H, Me, Et, Pr, or Bu.

Also disclosed are methods of depositing a Si-containing layer on a substrate.

At least one organosilane precursor disclosed above is introduced into a reactor having at least one substrate disposed therein. At least part of the organosilane precursor is deposited onto the at least one substrate to form a Si-containing layer using a vapor deposition method. The disclosed methods may have one or more of the following aspects:

introducing into the reactor a vapor comprising at least one second precursor;

an element of the at least one second precursor being selected from the group consisting of group 2, group 13, group 14, transition metal, lanthanides, and combinations thereof;

the element of the at least one second precursor being selected from Mg, Ca, Sr, Ba, Zr, Hf, Ti, Nb, Ta, Al, Si, Ge, Y, or lanthanides;

introducing into the reactor at least one co-reactant;

the co-reactant being selected from the group consisting of $O_2$, $O_3$, $H_2O$, $H_2O_2$, NO, $NO_2$, a carboxylic acid, and combinations thereof;

the co-reactant being water;

the co-reactant being ozone;

the co-reactant being plasma treated oxygen;

the Si-containing layer being a silicon oxide layer;

the co-reactant being selected from the group consisting of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkylsilanes (such as $Me_2SiH_2$, $Et_2SiH_2$, $MeSiH_3$, $EtSiH_3$), hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, $(SiMe_3)_2NH$), pyrazoline, pyridine, B-containing molecules (such as $B_2H_6$, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof;

the co-reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;

the co-reactant being plasma-treated;

the co-reactant being remote plasma-treated;

the co-reactant not being plasma-treated;

the co-reactant being $H_2$;

the co-reactant being $NH_3$;

the co-reactant being HCDS;

the co-reactant being PODS;

the co-reactant being tetrachlorosilane;

the co-reactant being trichlorosilane;

the co-reactant being hexachlorocyclohexasilane;

the vapor deposition process being a chemical vapor deposition process;

the vapor deposition process being an atomic layer deposition (ALD) process;

the vapor deposition processing being a spatial ALD process;

the silicon-containing layer being Si;

the silicon-containing layer being $SiO_2$;

the silicon-containing layer being SiN;

the silicon-containing layer being SiON;

the silicon-containing layer being SiCN; and the silicon-containing layer being SiCOH.

DESCRIPTION OF PREFERRED EMBODIMENTS

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

The disclosed organosilane precursors have the following formula:

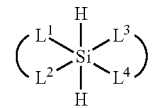

wherein each $L^1$, $L^2$, $L^3$, and $L^4$ is independently an oxygen or nitrogen atom, $L^1$ and $L^2$ and $L^3$ and $L^4$ being joined together via a carbon bridge having one to three carbon atoms; and $L^1$, $L^2$, and the carbon bridge and $L^3$, $L^4$, and the carbon bridge each form monoanionic ligands bonded to silicon. As illustrated in the formula, the $L^1$, $L^2$, $L^3$, and $L^4$ nitrogen or oxygen atoms are bonded to the silicon atom, resulting in a hexacoordinate Si (IV) center. The carbon atoms in the carbon bridge may be $sp^2$ hybridized, resulting in a delocalized charge across the monoanionic ligand. Alternatively, the carbon atoms in the carbon bridge may be either $sp^3$ hybridized or some combination of $sp^2$ and $sp^3$ hybridized, resulting in a negative charge on one of $L^1$ or $L^2$ and $L^3$ or $L^4$ resulting in a neutral charge on the other of $L^1$ or $L^2$ and $L^3$ or $L^4$. Each of the nitrogen, oxygen, and carbon atoms may independently be substituted by H, C1-C6 alkyl groups, aryl groups, or heterocycle groups.

The disclosed organosilane precursors are derived from different classes of ligand systems, such as diketiminate, diketonate, ketoiminate, amidinate, guanidinate, isoureate, and/or α-halo amidinate ligands. The specific design of these precursors may help improve volatility, reduce the melting point (liquids or very low melting solids), increase reactivity with water, and increase thermal stability for wider process window applications. The disclosed organosilane precursors may be more reactive than other $R_{4-x}SiL_x$ precursors due to hypercoordination at the silicon atom. In other words, although the silicon atom is +IV, the two hydrogen bonds and the monoanionic chelating ligands results in a total of 6 bonds to the silicon atom.

The hexacoordinate organosilane precursor contains two hydrogen atoms directly bonded to the Si atom. These Si—H bonds may help increase the volatility of the precursor. The disclosed organosilane precursors contain no Si-halogen bonds, which is important because halogens may damage other layers in the substrate (e.g., low k layers, copper interconnect layers, etc.). Additionally, in ALD processes, the two Si—H bonds of the disclosed precursors may help to provide a larger growth rate per cycle when compared to the analogous Si-halogen containing precursors because the H atoms occupy less surface area, resulting in more molecules on the substrate surface.

$L^1$, $L^2$, $L^3$ and $L^4$ may all be nitrogen atoms. Due to their increased nitrogen content when compared to the when any of $L^1$ through $L^4$ is an oxygen atom, these molecules may be used to produce silicon-containing films that also contain nitrogen, such as SiN, SiCN, SiON, MSiN, or MSiON, wherein M is an element such as Hf, Zr, Ti, Nb, Ta, or Ge, or to tune the amount of nitrogen in those films.

Exemplary organosilane precursors wherein $L^1$, $L^2$, $L^3$ and $L^4$ are all nitrogen atoms may have the following formula:

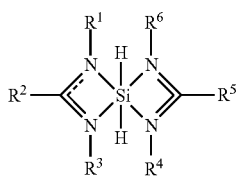

wherein $R^1$, $R^2$, $R^3$, $R^4$, $R^5$ and $R^6$ may each independently be H, a C1 to C6 alkyl group, or a C3-C20 aryl or heterocycle group. One of ordinary skill in the art will recognize that the use of hydrogen, alkyl, aryl or heterocycle groups having less carbon atoms (i.e., H, C1 or C2) will produce a molecule having higher volatility as compared to a molecule having alkyl, aryl or heterocycle groups with more carbons (i.e., C4+).

The bisamidinate precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[R^1NC(R^2)NR^3]$ (or Li(amd)), under atmosphere of nitrogen, the outlet of the mixing flask being connected to an oil bubbler to inhibit backflow of air and moisture. A second synthetic route to the disclosed amidinate precursors is by reaction of the protonated ligand ($R^1N=C(R^2)-NRH^3$) with either a neat or a hydrocarbon solution of a bis(dialkylamino)silane [$SiH_2(NR_2)_2$] performed under an inert atmosphere. Alternatively, the disclosed amidinate precursors may be synthesized by reaction of $SiH_nCl_{4-n}$ with two equivalents of the ligand compound (i.e., $Li[R^1NC(R^2)NR^3]$ or Li(amd)) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(amd), all of the starting materials are commercially available. The ligand compound may be synthesized by combining a hydrocarbon solution of metalorganic salt (i.e., alkyl lithium) to a hydrocarbon solution of the appropriate carbodiimide (i.e., $R^1N=C=NR^3$). Additional synthesis details are provided in the Examples.

Exemplary bisamidinate precursors include:

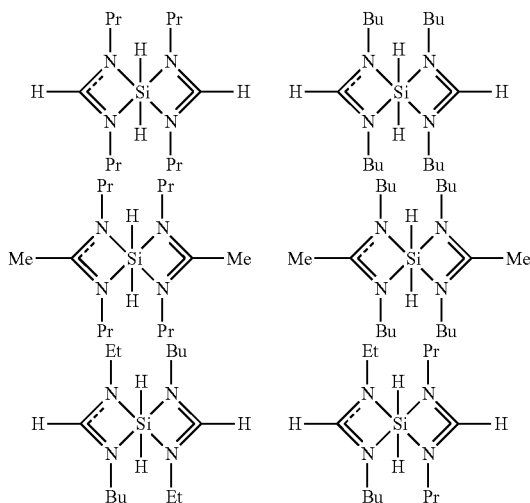

Exemplary organosilane precursors wherein $L^1$, $L^2$, $L^3$ and $L^4$ are all nitrogen atoms may have the following formula:

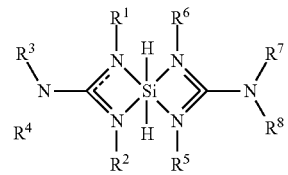

wherein $R^1$, $R^2$, $R^3$, $R^4$, $R^5$ and $R^6$ may each independently be H, a C1 to C6 alkyl group, or a C3-C20 aryl or heterocycle group. Due to their increased nitrogen content when compared to the other molecules, these molecules may be used to produce silicon-containing films that also contain nitrogen, such as SiN or SiON, or to tune the amount of nitrogen in a SiN or SiON containing film.

The guanidinate precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[R^1NC(NR^3R^4)NR^2]$ (or Li(gnd)), under atmosphere of nitrogen, the outlet of the mixing flask being connected to an oil bubbler to inhibit backflow of air and moisture. A second synthetic route to the disclosed guanidinate precursors is by reaction of the protonated ligand ($R^1N=C(NR^3R^4)-NR^2H$) with either a neat or a hydrocarbon solution of a bis(dialkylamino)silane [$SiH_2(NR_2)_2$] performed under an inert atmosphere. Alternatively, the disclosed guanidinate precursors may be synthesized by reaction of $SiH_nCl_{4-n}$ with two equivalents of the ligand compound (i.e., $Li[R^1NC(NR^3R^4)NR^2]$ or Li(gnd)) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(gnd), all of the starting materials are commercially available. The ligand compound may be synthesized by combining a hydrocarbon solution of metalorganic salt (i.e., amino lithium —$Li(NR^3R^4)$) to a hydrocarbon solution of the appropriate carbodiimide (i.e., $R^1N=C=NR^2$).

Exemplary bisguanidinate precursors include:

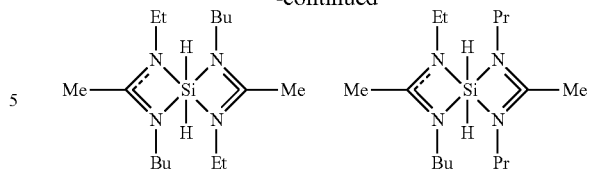

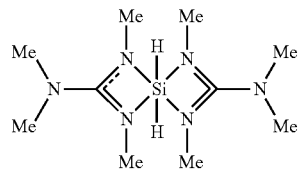

-continued

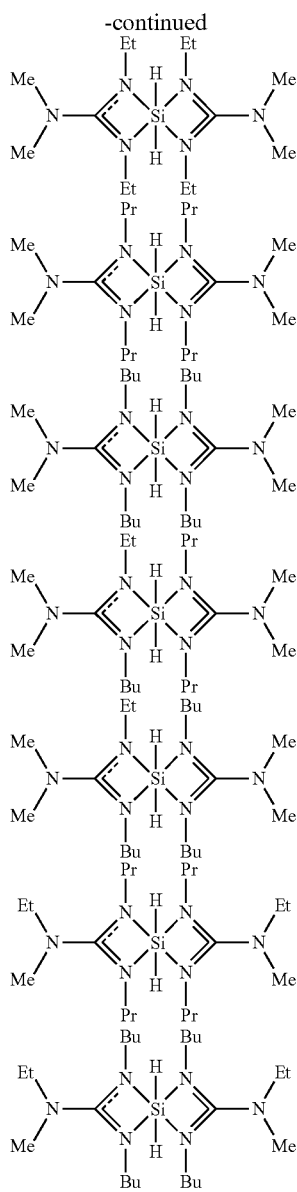

Exemplary organosilane precursors wherein $L^1$, $L^2$, $L^3$ and $L^4$ are all nitrogen atoms may have the following formula:

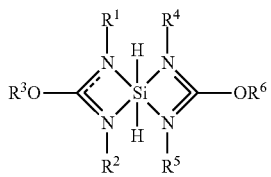

wherein $R^1$, $R^2$, $R^3$, $R^4$, $R^5$ and $R^6$ may each independently be H, a C1 to C6 alkyl group, or a C3-C20 aryl or heterocycle group. Due to their increased oxygen content when compared to the other molecules, these molecules may be used to produce silicon-containing films that also contain oxygen, such as $SiO_2$ or SiON, or to tune the amount of oxygen in a $SiO_2$ or SiON containing film.

The isoureate precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[R^1NC(OR^3)NR^2]$ (or Li(iso)), under atmosphere of nitrogen, the outlet of the mixing flask being connected to an oil bubbler to inhibit backflow of air and moisture. A second synthetic route to the disclosed isoureate precursors is by reaction of the protonated ligand ($R^1N=C(OR^3)$—$NR^2H$) with either a neat or a hydrocarbon solution of a dialkylaminosilane [$SiH_3(NR_2)$] performed under an inert atmosphere. Alternatively, the disclosed isoureate precursors may be synthesized by reaction of $SiH_nCl_{4-n}$ with a single equivalent of the ligand compound (i.e., $Li[R^1NC(OR^3)NR^2]$ or Li(iso)) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(iso), all of the starting materials are commercially available. The ligand compound may be synthesized by combining a hydrocarbon solution of metalorganic salt (i.e., alkoxy lithium —$Li(OR^3)$) to a hydrocarbon solution of the appropriate carbodiimide (i.e., $R^1N=C=NR^2$).

Exemplary bisisoureate precursors include:

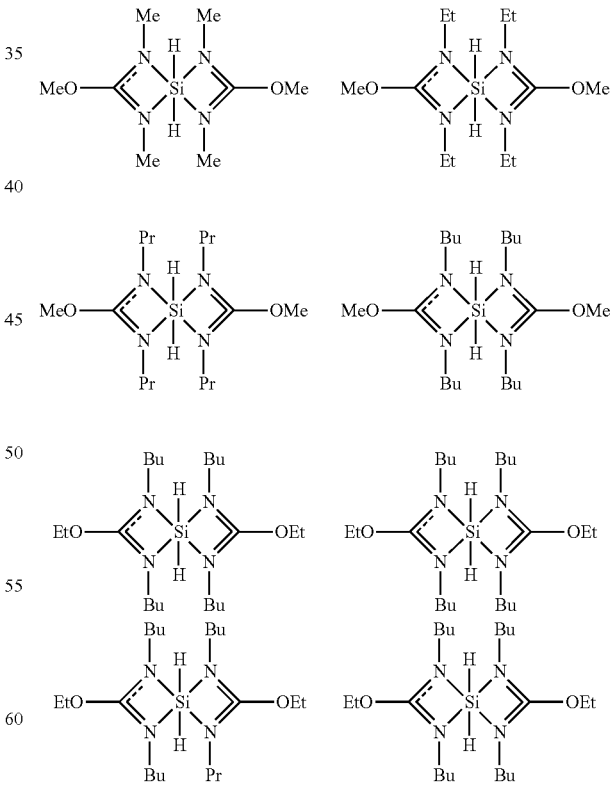

Exemplary organosilane precursors wherein $L^1$, $L^2$, $L^3$ and $L^4$ are all nitrogen atoms may have the following formula:

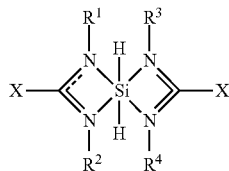

wherein $R^1$, $R^2$, $R^3$, and $R^4$ may each independently be H, a C1 to C6 alkyl group, or a C3-C20 aryl or heterocycle group, and each X may independently be Cl, Br, I, or F. Unlike the prior art compounds, the halogen atoms are bonded to the carbon backbone, not directly to the Si. As a result, halogen contamination of the substrate is minimized because the halogen atom will leave the reactor with the volatile haloamidinate by-product.

The alpha-haloamidinate precursors may be synthesized by combining a hydrocarbon solution of a disubstituted urea derivative $R^1HN$—(C=O)—$NHR^2$ with a hydrocarbon solution of O=$CX_2$ as described by Neubauer et al. (*Chemische Berichte*, 1964, 97(5), 1232-1245). A hydrocarbon solution of one molar equivalent of an appropriate base (such as potassium hexamethyldisilazide) is added to the reaction mixture and the resulting suspension filtered to remove metal salt byproducts. The resulting solution may be reacted with $SiH_2(aryl)_2$, wherein aryl can be phenyl, tolyl, or any other appropriate aryl substituent. The resulting mixture may be purified by fractional distillation.

Exemplary organosilane precursors wherein $L^1$, $L^2$, $L^3$ and $L^4$ are all nitrogen atoms may have the following formula:

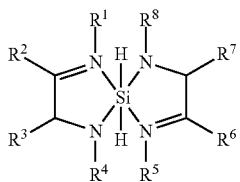

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group. The four carbon atoms may be $sp^2$ or $sp^3$ hybridized. The formula above illustrates an anionic charge localized at the "$L^2$" nitrogen atom. The "$L^1$" nitrogen atom having the double bond to $C(R^3)$ forms a dative bond to the silicon atom. However, one of ordinary skill in the art will recognize that the double bond may also be delocalized across the ring when the carbon atoms are $sp^2$ hybridized. If $R^1$ and $R^4$ are the same and $R^2$ and $R^3$ are the same (i.e., all Me, or $R^1$ and $R^4$=Me and $R^2$ and $R^3$=H), the resulting Fourier-transform Infra Red (FTIR) spectra for these molecules will produce one peak for both of the N atoms due to the delocalization of the electrons across the ligand.

Exemplary organosilane precursors wherein $L^1$, $L^2$, $L^3$ and $L^4$ are all nitrogen atoms may have the following formula:

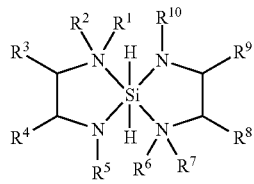

wherein $R^1$, $R^2$, $R^3$, $R^4$, $R^5$, $R^6$, $R^7$, $R^8$, $R^9$ and $R^{10}$ may each independently be H, a C1 to C6 alkyl group, or a C3-C20 aryl or heterocycle group. The four carbon atoms may be $sp^2$ or $sp^3$ hybridized. An anionic charge may be localized one of the nitrogen atoms. The second nitrogen atom may form a dative bond to the Si atom. Due to the unsymmetrical nature of the ligand, the three carbon atoms will produce different peaks in nuclear magnetic resonance (NMR) spectra.

The $H_2Si[RN(CR)_2NR]_2$ or $H_2Si[R_2N(CR)_2NR]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[RN(CR)_2NR]$ or $Li[R_2N(CR)_2NR]$, under atmosphere of nitrogen, the outlet of the mixing flask being connected to an oil bubbler to inhibit backflow of air and moisture. A second synthetic route to the disclosed $H_2Si[RN(CR)_2NR]_2$ or $H_2Si[R_2N(CR)_2NR]_2$ precursors is by reaction of the protonated ligand $RN(CR)_2NHR$ or $RHN(CR)_2NR_2$ with either a neat or a hydrocarbon solution of a bis(dialkylamino)silane $[SiH_2(NR_2)_2]$ performed under an inert atmosphere. Alternatively, the disclosed $H_2Si[RN(CR)_2 NR]_2$ or $H_2Si[R_2N(CR)_2NR]_2$ precursors may be synthesized by reaction of $SiH_nCl_{4-n}$ with two equivalents of the ligand compound (i.e., $Li[RN(CR)_2NR]$ or $Li[R_2N(CR)_2 NR]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN(CR)_2NR]$ or $Li[R_2N(CR)_2NR]$, all of the starting materials are commercially available. The ligand compound may be synthesized by combining a hydrocarbon solution of metalorganic salt (i.e., alkyl lithium) to a hydrocarbon solution of the appropriate diamine (i.e., $R^1N=CR^2$—$CR^3$—$NHR^4$, $R^1HN$—$CR^2$—$CR^3$—$NR^4R^5$).

Exemplary organosilane precursors wherein $L^1$, $L^2$, $L^3$ and $L^4$ are all nitrogen atoms may have the following formula:

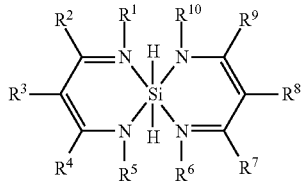

wherein $R^1$, $R^2$, $R^3$, $R^4$, $R^5$, $R^6$, $R^7$, $R^8$, $R^9$ and $R^{10}$ may each independently be H, a C1 to C6 alkyl group, or a C3-C20 aryl or heterocycle group. The six carbon atoms are $sp^2$ hybridized. If $R^1$ and $R^5$ are the same and $R^2$ and $R^4$ are the same (i.e., all Me, or $R^1$ and $R^5$=Me and $R^2$ and $R^4$=H), the resulting Fourier-Transform Infra Red (FTIR) spectra for these molecules will produce one peak for both of the N atoms due to the delocalization of the electrons across the ligand.

Exemplary bis(β-diketiminato)silane precursors include:

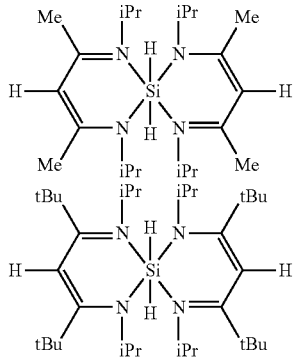

Exemplary organosilane precursors wherein $L^1$, $L^2$, $L^3$ and $L^4$ are all nitrogen atoms may have the following formula:

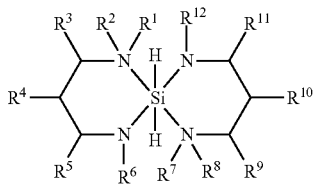

wherein $R^1$, $R^2$, $R^3$, $R^4$, $R^5$, $R^6$, $R^7$, $R^8$, $R^9$, $R^{10}$, $R^{11}$ and $R^{12}$ may each independently be H, a C1 to C6 alkyl group, or a C3-C20 aryl or heterocycle. The six carbon atoms may be $sp^2$ or $sp^a$ hybridized. An anionic charge may be localized at the "$L^2$" nitrogen atom. The "$L^1$" nitrogen atom may form a dative bond to the Si atom. Due to the unsymmetrical nature of the ligand, the three carbon atoms will produce different peaks in nuclear magnetic resonance (NMR) spectra.

The $H_2Si[RN(CR)_3NR]_2$ or $H_2Si[R_2N(CR)_3NR]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[RN(CR)_3NR]$ or $Li[R_2N(CR)_3NR]$, under atmosphere of nitrogen, the outlet of the mixing flask being connected to an oil bubbler to inhibit backflow of air and moisture. A second synthetic route to the disclosed $H_2Si[RN(CR)_3NR]_2$ or $H_2Si[R_2N(CR)_3NR]_2$ precursors is by reaction of the protonated ligand $RN(CR)_3NHR$ or $RHN(CR)_3NR_2$ with either a neat or a hydrocarbon solution of a bis(dialkylamino)silane $[SiH_2(NR_2)_2]$ performed under an inert atmosphere. Alternatively, the disclosed $H_2Si[RN(CR)_3NR]_2$ or $H_2Si[R_2N(CR)_3NR]_2$ precursors may be synthesized by reaction of $SiH_nCl_{4-n}$ with two equivalents of the ligand compound (i.e., $Li[RN(CR)_3NR]$ or $Li[R_2N(CR)_3NR]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN(CR)_3NR]$ or $Li[R_2N(CR)_3NR]$, all of the starting materials are commercially available. The ligand compound may be synthesized by combining a hydrocarbon solution of metalorganic salt (i.e., alkyl lithium) to a hydrocarbon solution of the appropriate diamine (i.e., $R^1N=CR^2-CR^3-CR^4-NHR^5$, $R^1N=CR^2-CR^3=CR^4-NHR^5$, $R^1HN-CR^2-CR^3-CR^4-NR^5R^6$).

$L^1$, $L^2$, $L^3$, and $L^4$ may all be oxygen atoms. Due to the increased oxygen content when compared to the when any of $L^1$ through $L^4$ is a nitrogen atom, these molecules may be used to produce silicon-containing films that also contain oxygen, such as $SiO_2$, $SiOC$, or $SiON$, or to tune the amount of oxygen in a $SiO_2$, $SiOC$, or $SiON$ containing film.

Exemplary organosilane precursors wherein $L^1$, $L^2$, $L^3$, and $L^4$ are all oxygen atoms may have the following formula:

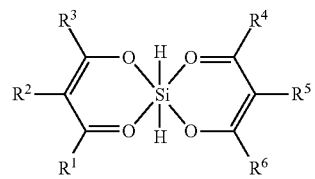

wherein $R^1$, $R^2$, $R^3$, $R^4$, $R^5$, and $R^6$ may each independently be H, a C1 to C6 alkyl group, or a C3-C20 aryl or heterocycle group. The three carbon atoms are $sp^2$ hybridized. If $R^1$, $R^3$, $R^4$, and $R^6$ are the same (i.e., each Me), the resulting nuclear magnetic transform Fourier-Transform Infra Red (FTIR) spectra for these molecules will produce one peak for the O atoms due to the delocalization of the electrons across the ligand.

Exemplary bis(diketonato)silane precursors include:

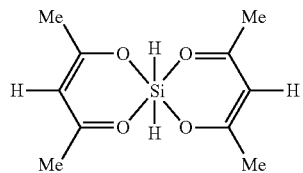

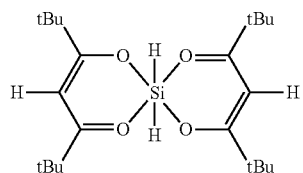

Exemplary organosilane precursors wherein $L^1$, $L^2$, $L^3$, and $L^4$ are all oxygen atoms may have the following formula:

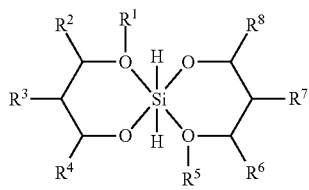

wherein $R^1$, $R^2$, $R^3$, and $R^4$ may each independently be H, a C1 to C6 alkyl group, or a C3-C20 aryl or heterocycle group. Each carbon atom may be $sp^2$ or $sp^3$ hybridized. An anionic charge may be localized at one of the oxygen atoms. The other oxygen atom may form a dative bond to the Si atom. Due to the unsymmetrical nature of the ligand, the three carbon atoms will produce different peaks in nuclear magnetic resonance (NMR) spectra.

Exemplary silyl bis(3-methoxy-1-propanolato-O,O') precursors include:

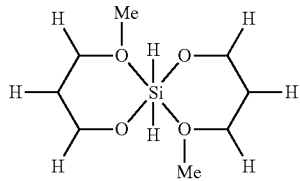

The $H_2Si[O(CR)_3O]_2$ and $H_2Si[RO(CR)_3O]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[O(CR)_3O]$ or $Li[RO(CR)_3O]$ under atmosphere of nitrogen, the outlet of the mixing flask being connected to an oil bubbler to inhibit backflow of air and moisture. A second synthetic route to the disclosed $H_2Si[O(CR)_3O]_2$ and $H_2Si[RO(CR)_3O]_2$ precursors is by reaction of the protonated ligand ($HO(CR)_3O$ or $RO(CR)_3OH$) with either a neat or a hydrocarbon solution of a bis(dialkylamino)silane [$SiH_2(NR_2)_2$] performed under an inert atmosphere. Alternatively, the disclosed $H_2Si[O(CR)_3O]_2$ and $H_2Si[RO(CR)_3O]_2$ precursors may be synthesized by reaction of $SiH_nCl_{4-n}$ with a two equivalents of the ligand compound (i.e., $Li[O(CR)_3O]$ or $Li[RO(CR)_3O]$) and subsequent reduction using a selected metal hydride such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[O(CR)_3O]$ or $Li[RO(CR)_3O]$ all of the starting materials are commercially available. The ligand compound may be synthesized by combining a hydrocarbon solution of metalorganic salt (i.e., alkyl lithium) to a hydrocarbon solution of the appropriate hydroxy ketone or hydroxy ether (i.e., $R^1O-CR^2-CR^3-CR^4-OH$, $O=CR^1-CR^2-CR^3-OH$, and $O=CR^1-CR^2=CR^3-OH$).

Exemplary organosilane precursors wherein $L^1$, $L^2$, $L^3$, and $L^4$ are all oxygen atoms may have the following formula:

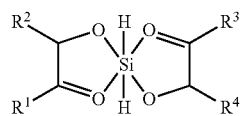

wherein $R^1$ and $R^2$ may each independently be H, a C1 to C6 alkyl group, or a C3-C20 aryl or heterocycle group. The four carbon atoms may be $sp^2$ or $sp^3$ hybridized. The formula above illustrates an anionic charge localized at the single bonded oxygen atom. The oxygen atom having the double bond to $C(R^1)$ forms a dative bond to the silicon atom. However, one of ordinary skill in the art will recognize that the double bond may also be delocalized across the ring when the carbon atoms are $sp^2$ hybridized. If $R^1$ and $R^2$ are the same (i.e., both Me), the resulting Fourier-transform Infra Red (FTIR) spectra for the delocalized molecules will produce one peak for both of the O atoms due to the delocalization of the electrons across the ligand.

Exemplary ketosilylether precursors include:

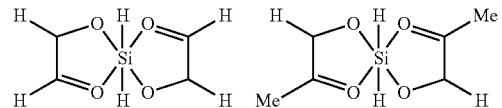

Exemplary organosilane precursors wherein $L^1$, $L^2$, $L^3$, and $L^4$ are all oxygen atoms may have the following formula:

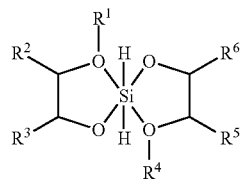

wherein $R^1$, $R^2$, and $R^3$ may each independently be H, a C1 to C6 alkyl group, or a C3-C20 aryl or heterocycle group. The four carbon atoms may be $sp^2$ or $sp^3$ hybridized. An anionic charge may be localized at one of the oxygen atoms. The other oxygen atom may form a dative bond to the Si atom. Due to the unsymmetrical nature of the ligand, the two carbon atoms will produce different peaks in nuclear magnetic resonance (NMR) spectra.

Exemplary silyl bis(2-alkoxy-1-ethanolato-O,O') precursors include:

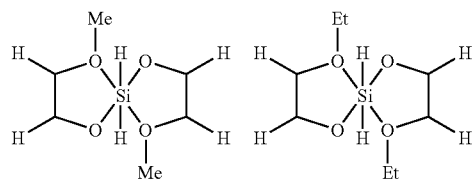

The $H_2Si[O(CR)_2O]_2$ and $H_2Si[RO(CR)_2O]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[O(CR)_2O]$ or $Li[RO(CR)_2O]$ under atmosphere of nitrogen, the outlet of the mixing flask being connected to an oil bubbler to inhibit backflow of air and moisture. A second synthetic route to the disclosed $H_2Si[O(CR)_2O]_2$ and $H_2Si[RO(CR)_2O]_2$ precursors is by reaction of the protonated ligand ($HO(CR)_2O$ or $RO(CR)_2OH$) with either a neat or a hydrocarbon solution of a bis(dialkylamino)silane [$SiH_2(NR_2)_2$] performed under an inert atmosphere. Alternatively, the disclosed $H_2Si[O(CR)_2O]_2$ and $H_2Si[RO(CR)_2O]_2$ precursors may be synthesized by reaction of $SiH_nCl_{4-n}$ with two equivalents of the ligand compound (i.e., $Li[O(CR)_2O]$ or $Li[RO(CR)_2O]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[O(CR)_2O]$ or $Li[RO(CR)_2O]$ all of the starting materials are commercially available. The ligand compound may be synthesized by combining a hydrocarbon solution of metalorganic salt (i.e., alkyl lithium) to a hydrocarbon solution of the appropriate hydroxy ketone or hydroxy ether (i.e., $R^1O-CR^2-CR^3-OH$ or $O=CR^1-CR^2-OH$).

Exemplary organosilane precursors wherein $L^1$, $L^2$, $L^3$, and $L^4$ are all oxygen atoms may have the following formula:

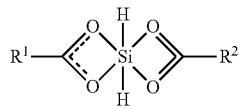

wherein $R^1$ and $R^2$ may be H, a C1 to C6 alkyl group, or a C3-C20 aryl or heterocycle group. The carbon atom is $sp^2$ hybridized.

Exemplary bis(acetato)silane precursors include:

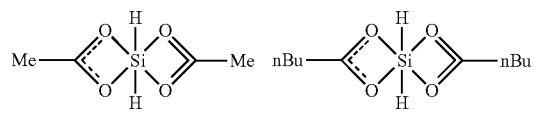

The $H_2Si[OC(R^2)O]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[OC(R^2)O]$, under atmosphere of nitrogen, the outlet of the mixing flask being connected to an oil bubbler to inhibit backflow of air and moisture. A second synthetic route to the disclosed $H_2Si[OC(R^2)O]_2$ precursors is by reaction of the protonated ligand ($HOC(R^2)=O$) with either a neat or a hydrocarbon solution of a bis(dialkylamino)silane [$SiH_2(NR_2)_2$] performed under an inert atmosphere. Alternatively, the disclosed $H_2Si[OC(R^2)O]_2$ precursors may be synthesized by reaction of $SiH_nCl_{4-n}$ with two equivalents of the ligand compound (i.e., $Li[OC(R^2)O]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[OC(R^2)O]$ all of the starting materials are commercially available. The ligand compound may be synthesized by bubbling carbon dioxide (i.e., $O=C=O$) into a hydrocarbon solution of metalorganic salt (i.e., alkyl lithium).

$L^1$ and $L^4$ may both be nitrogen atoms and $L^2$ and $L^3$ may both be oxygen atoms. Due to their increased nitrogen content when compared to the when $L^1$ and $L^4$ are oxygen atoms, these molecules may be used to produce silicon-containing films that also contain nitrogen, such as SiN, SiCN, SiON, MSiN, or MSiON, wherein M is an element such as Hf, Zr, Ti, Nb, Ta, or Ge, or to tune the amount of nitrogen in those films.

Exemplary organosilane precursors wherein $L^1$ and $L^4$ are nitrogen atoms and $L^2$ and $L^3$ are oxygen atoms may have the following formula:

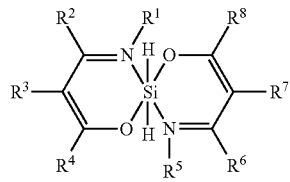

wherein $R^1$, $R^2$, $R^3$, and $R^4$ may each independently be H, a C1 to C6 alkyl group, or a C3-C20 aryl or heterocycle group. The six carbon atoms are $sp^2$ hybridized and the electrons are delocalized across the ligand.

Exemplary organosilane precursors wherein $L^1$ and $L^4$ are nitrogen atoms and $L^2$ and $L^3$ are oxygen atoms may have the following formula:

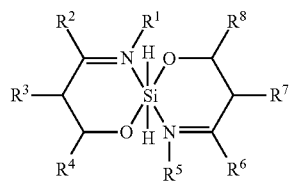

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group. The six carbon atoms may be $sp^2$ or $sp^3$ hybridized. An anionic charge may be localized at the oxygen atom. The nitrogen atom may form a dative bond to the Si atom. Due to the unsymmetrical nature of the ligand, the three carbon atoms will produce different peaks in nuclear magnetic resonance (NMR) spectra.

Exemplary organosilane precursors wherein $L^1$ and $L^4$ are nitrogen atoms and $L^2$ and $L^3$ are oxygen atoms may have the following formula:

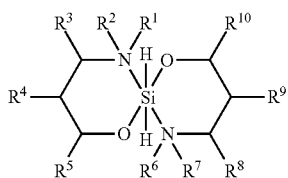

wherein $R^1$, $R^2$, $R^3$, $R^4$, $R^5$, $R^6$, $R^7$, $R^8$, $R^9$ and $R^{10}$ may each independently be H, a C1 to C6 alkyl group, or a C3-C20 aryl or heterocycle group. The six carbon atoms may be $sp^2$ or $sp^3$ hybridized. An anionic charge may be localized at the oxygen atom. The nitrogen atom may form a dative bond to the Si atom. Due to the unsymmetrical nature of the ligand, the three carbon atoms will produce different peaks in nuclear magnetic resonance (NMR) spectra.

Exemplary β-aminosilylether precursors include:

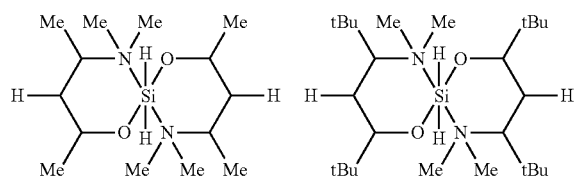

Exemplary organosilane precursors wherein $L^1$ and $L^4$ are nitrogen atoms and $L^2$ and $L^3$ are oxygen atoms may have the following formula:

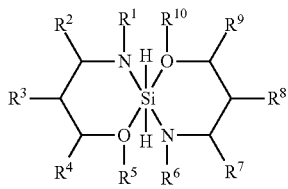

wherein $R^1$, $R^2$, $R^3$, $R^4$, $R^5$, $R^6$, $R^7$, $R^8$, $R^9$ and $R^{10}$ may each independently be H, a C1 to C6 alkyl group, or a C3-C20 aryl or heterocycle group. The six carbon atoms may be $sp^2$ or $sp^3$ hybridized. An anionic charge may be localized at the nitrogen atom. The oxygen atom may form a dative bond to the Si atom. Due to the unsymmetrical nature of the ligand, the three carbon atoms will produce different peaks in nuclear magnetic resonance (NMR) spectra.

Exemplary organosilane precursors wherein $L^1$ and $L^4$ are nitrogen atoms and $L^2$ and $L^3$ are oxygen atoms may have the following formula:

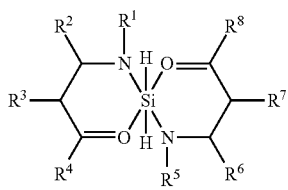

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group. The six carbon atoms may be $sp^2$ or $sp^3$ hybridized. An anionic charge may be localized at the nitrogen atom. The oxygen atom may form a dative bond to the Si atom. Due to the unsymmetrical nature of the ligand, the three carbon atoms will produce different peaks in nuclear magnetic resonance (NMR) spectra.

The $H_2Si[RN(CR)_3O]_2$, $H_2Si[R_2N(CR)_3O]_2$, and $H_2Si[RN(CR)_3OR]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[RN(CR)_3O]$, $Li[R_2N(CR)_3O]$, or $Li[RN(CR)_3OR]$, under atmosphere of nitrogen, the outlet of the mixing flask being connected to an oil bubbler to inhibit backflow of air and moisture. A second synthetic route to the disclosed $H_2Si[RN(CR)_3O]_2$, $H_2Si[R_2N(CR)_3O]_2$, and $H_2Si[RN(CR)_3OR]_2$ precursors is by reaction of the protonated ligand ($RN(CR)_3OH$, $R_2N(CR)_3OH$, or $RHN(CR)_3OR$ with either a neat or a hydrocarbon solution of a bis(dialkylamino)silane $[SiH_2(NR_2)_2]$ performed under an inert atmosphere. Alternatively, the disclosed $H_2Si[RN(CR)_3O]_2$, $H_2Si[R_2N(CR)_3O]_2$, and $H_2Si[RN(CR)_3OR]_2$ precursors may be synthesized by reaction of $SiH_nCl_{4-n}$ with two equivalents of the ligand compound (i.e., $Li[RN(CR)_3O]$, $Li[R_2N(CR)_3O]$, or $Li[RN(CR)_3OR]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN=CR(CR)_2O]$, $Li[R_2N(CR)_3O]$, or $Li[RN(CR)_3OR]$ all of the starting materials are commercially available. The ligand compound may be synthesized by combining a hydrocarbon solution of metalorganic salt (i.e., alkyl lithium) to a hydrocarbon solution of the appropriate hydroxy amine or hydroxy imine (i.e., $R^1N=CR^2-CR^3-CR^4-OH$, $R^1N=CR^2-CR^3-CR^4-OH$, $R^1R^2N-CR^3-CR^4-CR^5-OH$, $R^1HN-CR^2-CR^3-CR^4-OR^5$, or $R^1HN-CR^3-CR^4-CR^5=O$).

Exemplary organosilane precursors wherein $L^1$ and $L^4$ are nitrogen atoms and $L^2$ and $L^3$ are oxygen atoms may have the following formula:

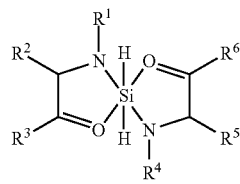

wherein $R^1$, $R^2$, $R^3$, $R^4$, $R^5$ and $R^6$ may each independently be H, a C1 to C6 alkyl group, or a C3-C20 aryl or heterocycle group. The four carbon atoms may be $sp^2$ or $sp^a$ hybridized. The formula above illustrates an anionic charge localized at the nitrogen atom. The oxygen atom having the double bond to $C(R^3)$ forms a dative bond to the silicon atom. However, one of ordinary skill in the art will recognize that the double bond may also be delocalized across the ring when the carbon atoms are $sp^2$ hybridized.

Exemplary organosilane precursors wherein $L^1$ and $L^4$ are nitrogen atoms and $L^2$ and $L^3$ are oxygen atoms may have the following formula:

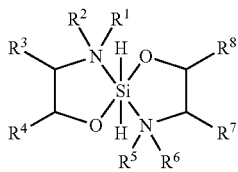

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group. The four carbon atoms may be $sp^2$ or $sp^3$ hybridized. An anionic charge may be localized at the oxygen atom. The nitrogen atom may form a dative bond to the Si atom. Due to the unsymmetrical nature of the ligand, the two carbon atoms will produce different peaks in nuclear magnetic resonance (NMR) spectra.

Exemplary α-aminosilylether precursors include:

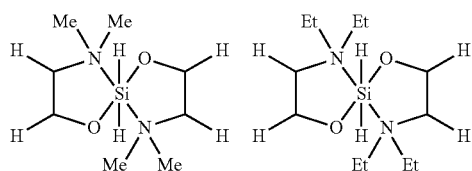

Exemplary organosilane precursors wherein $L^1$ and $L^4$ are nitrogen atoms and $L^2$ and $L^3$ are oxygen atoms may have the following formula:

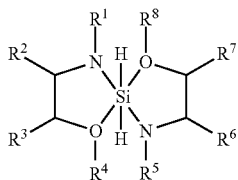

wherein $R^1$, $R^2$, $R^3$, $R^4$, $R^5$, $R^6$, $R^7$ and $R^8$ may each independently be H, a C1 to C6 alkyl group, or a C3-C20 aryl or heterocycle group. The four carbon atoms may be $sp^2$ or $sp^3$ hybridized. An anionic charge may be localized at the nitrogen atom. The oxygen atom may form a dative bond to the Si atom. Due to the unsymmetrical nature of the ligand, the three carbon atoms will produce different peaks in nuclear magnetic resonance (NMR) spectra.

Exemplary organosilane precursors wherein $L^1$ and $L^4$ are nitrogen atoms and $L^2$ and $L^3$ are oxygen atoms may have the following formula:

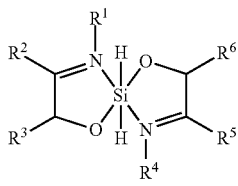

wherein $R^1$, $R^2$, $R^3$, $R^4$, $R^5$ and $R^6$ may each independently be H, a C1 to C6 alkyl group, or a C3-C20 aryl or heterocycle group. The four carbon atoms may be $sp^2$ or $sp^a$ hybridized. An anionic charge may be localized at the oxygen atom. The nitrogen atom may form a dative bond to the Si atom. Due to the unsymmetrical nature of the ligand, the three carbon atoms will produce different peaks in nuclear magnetic resonance (NMR) spectra.

The $H_2Si[RN(CR)_2O]_2$, $H_2Si[R_2N(CR)_2O]_2$, and $H_2Si[RN(CR)_2OR]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as $Li[RN(CR)_2O]$, $Li[R_2N(CR)_2O]$, or $Li[RN(CR)_2OR]$, under atmosphere of nitrogen, the outlet of the mixing flask being connected to an oil bubbler to inhibit backflow of air and moisture. A second synthetic route to the disclosed $H_2Si[RN(CR)_2O]_2$, $H_2Si[R_2N(CR)_2O]_2$, and $H_2Si[RN(CR)_2OR]_2$ precursors is by reaction of the protonated ligand ($RN(CR)_2OH$, $R_2N(CR)_2OH$, or $RHN(CR)_2OR$ with either a neat or a hydrocarbon solution of a bis(dialkylamino)silane $[SiH_2(NR_2)_2]$ performed under an inert atmosphere. Alternatively, the disclosed $H_2Si[RN(CR)_2O]_2$, $H_2Si[R_2N(CR)_2O]_2$, and $H_2Si[RN(CR)_2OR]_2$ precursors may be synthesized by reaction of $SiH_nCl_{4-n}$ with two equivalents of the ligand compound (i.e., $Li[RN(CR)_2O]$, $Li[R_2N(CR)_2O]$, or $Li[RN(CR)_2OR]$) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN(CR)_2O]$, $Li[R_2N(CR)_2O]$, or $Li[RN(CR)_2OR]$ all of the starting materials are commercially available. The ligand compound may be synthesized by combining a hydrocarbon solution of metalorganic salt (i.e., alkyl lithium) to a hydrocarbon solution of the appropriate hydroxy amine or hydroxy imine (i.e., $R^1N=CR^2-CR^3-OH$, $R^1R^2N-CR^3-CR^4-OH$, $R^1HN-CR^2-CR^3-OR^4$, or $R^1HN-CR^2-CR^3=O$).

Exemplary organosilane precursors wherein $L^1$ and $L^4$ are nitrogen atoms and $L^2$ and $L^3$ are oxygen atoms may have the following formula:

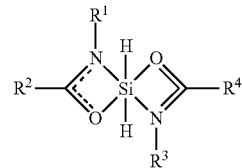

wherein $R^1$, $R^2$, $R^3$ and $R^4$ may each independently be H, a C1 to C6 alkyl group, or a C3-C20 aryl or heterocycle group. The carbon atom is $sp^2$ hybridized. Exemplary bis(N-alkylacetamidinato)silane precursors include:

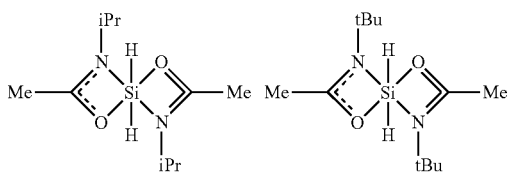

The $H_2Si[R^1NC(R^2)O]_2$ precursors may be synthesized by combining a hydrocarbon solution of $SiX_2H_2$, wherein X is Cl, Br, I, or triflate ($SO_3CF_3^-$), with a neat or hydrocarbon solution of the ligand compound, such as Li[$R^1NC(R^2)O$], under atmosphere of nitrogen, the outlet of the mixing flask being connected to an oil bubbler to inhibit backflow of air and moisture. A second synthetic route to the disclosed $H_2Si[R^1NC(R^2)O]_2$ precursors is by reaction of the protonated ligand ($R^1N$=$C(R^2)OH$) with either a neat or a hydrocarbon solution of a bis(dialkylamino)silane [$SiH_2(NR_2)]_2$ performed under an inert atmosphere. Alternatively, the disclosed $H_2Si[R^1NC(R^2)O]_2$ precursors may be synthesized by reaction of $SiH_nCl_{4-n}$ with two equivalents of the ligand compound (i.e., Li[$R^1NC(R^2)O$]) and subsequent reduction using a selected metal hydride, such as LAH (lithium aluminum hydride). In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li[$R^1NC(R^2)O$], all of the starting materials are commercially available. The ligand compound may be synthesized by combining a hydrocarbon solution of metalorganic salt (i.e., alkyl lithium) to a hydrocarbon solution of the appropriate isocyanate (i.e., $R^1N$=$C$=$O$).

To ensure process reliability, the hexacoordinate silicon-containing molecule may be purified by continuous or fractional batch distillation or sublimation prior to use to a purity ranging from approximately 95% w/w to approximately 100% w/w, preferably ranging from approximately 99% w/w to approximately 100% w/w. The hexacoordinate silicon-containing precursor may contain any of the following impurities: mono-, tris-, or tetra-substituted analogs; solvents; chlorinated metal compounds; or other reaction products. Preferably, the total quantity of these impurities is below 0.1% w/w.

The concentration of each of hexane, substituted hexane, pentane, substituted pentane, dimethyl ether, or anisole in the purified hexacoordinate silicon-containing molecule may range from approximately 0% w/w to approximately 5% w/w, preferably from approximately 0% w/w to approximately 0.1% w/w. Solvents may be used in the precursor's synthesis. Separation of the solvents from the precursor may be difficult if both have similar boiling points. Cooling the mixture may produce solid precursor in liquid solvent, which may be separated by filtration. Vacuum distillation may also be used, provided the precursor product is not heated above approximately its decomposition point.

In one embodiment the disclosed organosilane precursor contains less than 5% v/v, preferably less than 1% v/v, more preferably less than 0.1% v/v, and even more preferably less than 0.01% v/v of any of its mono-, tris-, or tetra-substituted analogs, reactants, or other reaction products. This embodiment may provide better process repeatability. This embodiment may be produced by distillation of the hexacoordinate organosilane precursor. In an alternate embodiment, the disclosed organosilane precursor may contain between 5% v/v and 50% v/v of one or more of its mono-, tris-, or tetra-substituted analogs, reactants, or other reaction products, particularly when the mixture provides improved process parameters or isolation of the target compound is too difficult or expensive. For example, a mixture of reaction products may produce a stable, liquid mixture suitable for vapor deposition.

The concentration of trace metals and metalloids in the purified hexacoordinate silicon-containing molecule may each range from approximately 0 ppb to approximately 100 ppb, and more preferably from approximately 0 ppb to approximately 10 ppb. The concentration of X (wherein X=Cl, Br, I, or F) in the purified hexacoordinate silicon-containing molecule may range from approximately 0 ppm to approximately 100 ppm and more preferably from approximately 0 ppm to approximately 10 ppm.

Also disclosed are methods of using the disclosed organosilane precursors for vapor deposition methods. The disclosed methods provide for the use of the organosilane precursors for deposition of silicon-containing films. The disclosed methods may be useful in the manufacture of semiconductor, photovoltaic, LCD-TFT, or flat panel type devices. The method includes: introducing the vapor of the disclosed organosilane precursors into a reactor having at least one substrate disposed therein: and using a vapor deposition process to deposit at least part of the disclosed organosilane precursor onto the substrate to form a Si-containing layer.

The disclosed methods also provide for forming a bimetal-containing layer on a substrate using a vapor deposition process and, more particularly, for deposition of $SiMO_x$ films, wherein x may be 0-4 and M is Ta, Hf, Nb, Mg, Al, Sr, Y, Ba, Ca, As, Sb, Bi, Sn, Pb, Co, lanthanides (such as Er), or combinations thereof.

The disclosed methods of forming silicon-containing layers on substrates may be useful in the manufacture of semiconductor, photovoltaic, LCD-TFT, or flat panel type devices. The disclosed organosilane precursors may deposit Si-containing films using any vapor deposition methods known in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The disclosed methods may also be used in the flowable PECVD deposition processes described in U.S. Pat. App. Pub. No. 2014/0051264 to Applied Materials, Inc., the contents of which is incorporated herein in its entirety. The deposition method is preferably ALD, spatial ALD, or PE-ALD.

The vapor of the organosilane precursor is introduced into a reaction chamber containing at least one substrate. The temperature and the pressure within the reaction chamber and the temperature of the substrate are held at conditions suitable for vapor deposition of at least part of the organosilane precursor onto the substrate. In other words, after introduction of the vaporized precursor into the chamber, conditions within the chamber are such that at least part of the vaporized precursor is deposited onto the substrate to form the silicon-containing film. A co-reactant may also be used to help in formation of the Si-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 300° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, Ge, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper layers, tungsten layers or metal layers (e.g. platinum, palladium, nickel, rhodium, or gold). The wafers may include barrier layers, such as manganese, manganese oxide, tantalum, tantalum nitride, etc. Plastic layers, such as poly(3,4-ethylenedioxythiophene)poly(styrenesulfonate) [PEDOT:PSS] may also be used. The layers may be planar or patterned. In some embodiments, the substrate may be a patterned photoresist film made of hydrogenated carbon, for example $CH_x$, wherein x is greater than zero (e.g., $x \leq 4$). In some embodiments, the substrate may include layers of oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN) that are used as an oxygen barrier between copper and the low-k layer. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. The actual substrate utilized may also depend upon the specific precursor embodiment utilized. In many instances though, the preferred substrate utilized will be selected from hydrogenated carbon, TiN, SRO, Ru, and Si type substrates, such as polysilicon or crystalline silicon substrates.

The disclosed organosilane precursors may be supplied either in neat form or in a blend with a suitable solvent, such as toluene, ethyl benzene, xylene, mesitylene, decane, dodecane, octane, hexane, pentane, tertiary amines, acetone, tetrahydrofuran, ethanol, ethylmethylketone, 1,4-dioxane, or others. The disclosed precursors may be present in varying concentrations in the solvent. For example, the resulting concentration may range from approximately 0.05 M to approximately 2 M.

The neat or blended organosilane precursors are introduced into a reactor in vapor form by conventional means, such as tubing and/or flow meters. The precursor in vapor form may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, or $N_2$, and mixtures thereof. Bubbling with a carrier gas may also remove any dissolved oxygen present in the neat or blended precursor solution. The carrier gas and precursor are then introduced into the reactor as a vapor.

If necessary, the container may be heated to a temperature that permits the organosilane precursor to be in its liquid phase and to have a sufficient vapor pressure. The container may be maintained at temperatures in the range of, for example, 0-150° C. Those skilled in the art recognize that the temperature of the container may be adjusted in a known manner to control the amount of organosilane precursor vaporized.

In addition to the disclosed precursor, a reaction gas may also be introduced into the reactor. The reaction gas may be an oxidizing agent such as one of $O_2$; $O_3$; $H_2O$; $H_2O_2$; oxygen containing radicals such as O. or OH.; NO; $NO_2$; carboxylic acids such as formic acid, acetic acid, propionic acid; radical species of NO, $NO_2$, or the carboxylic acids; para-formaldehyde; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Preferably, when an ALD process is performed, the co-reactant is plasma treated oxygen, ozone, or combinations thereof. When an oxidizing gas is used, the resulting silicon containing film will also contain oxygen.

Alternatively, the reaction gas may be a reducing agent such as one of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkylsilanes (such as $(CH_3)_2SiH_2$, $(C_2H_5)_2SiH_2$, $(CH_3)SiH_3$, $(C_2H_5)SiH_3$), hydrazines (such as $N_2H_4$, $MeHNNH_2$, MeHNNHMe), organic amines (such as $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$), pyrazoline, pyridine, B-containing molecules (such as $B_2H_6$, 9-borabicyclo[3,3,1]none, trimethylboron, triethylboron, borazine), alkyl metals (such as trimethylaluminum, triethylaluminum, dimethylzinc, diethylzinc), radical species thereof, and mixtures thereof. Preferably, the reducing agent is $H_2$, $NH_3$, $SiH_4$, $Si_2H_6$, $Si_3H_8$, SiH$_2$Me$_2$, SiH$_2$Et$_2$, N(SiH$_3$)$_3$, hydrogen radicals thereof, or mixtures thereof. When a reducing agent is used, the resulting silicon containing film may be pure Si.

The reaction gas may be treated by a plasma, in order to decompose the reaction gas into its radical form. N$_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

When the desired silicon-containing film also contains another element, such as, for example and without limitation, Ta, Hf, Nb, Mg, Al, Sr, Y, Ba, Ca, As, Sb, Bi, Sn, Pb, Co, lanthanides (such as Er), or combinations thereof, the co-reactants may include a metal-containing precursor which is selected from, but not limited to, metal alkyls, such as Ln(RCp)$_3$ or Co(RCp)$_2$, metal amines, such as Nb(Cp)(NtBu)(NMe$_2$)$_3$ and any combination thereof.

The disclosed organosilane precursors may also be used with a halosilane or polyhalodisilane, such as hexachlorodisilane, pentachlorodisilane, or tetrachlorodisilane, or octachlorotrisilane and one or more co-reactant gases to form SiN or SiCN films, as disclosed in PCT Publication Number WO2011/123792, the entire contents of which are incorporated herein in their entireties.

The organosilane precursor and one or more co-reactants may be introduced into the reaction chamber simultaneously (chemical vapor deposition), sequentially (atomic layer deposition), or in other combinations. For example, the organosilane precursor may be introduced in one pulse and two additional metal sources may be introduced together in a separate pulse [modified atomic layer deposition]. Alternatively, the reaction chamber may already contain the co-reactant prior to introduction of the organosilane precursor. The co-reactant may be passed through a plasma system localized or remotely from the reaction chamber, and decomposed to radicals. Alternatively, the organosilane precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s. In another alternative, the organosilane precursor and one or more co-reactants may be simultaneously sprayed from a shower head under which a susceptor holding several wafers is spun (spatial ALD).

In one non-limiting exemplary atomic layer deposition type process, the vapor phase of a organosilane precursor is introduced into the reaction chamber, where it is contacted with a suitable substrate. Excess organosilane precursor may then be removed from the reaction chamber by purging and/or evacuating the reaction chamber. An oxygen source is introduced into the reaction chamber where it reacts with the absorbed organosilane precursor in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal oxide film (i.e., SiMO$_x$, wherein x may be 0-4 and M is Ta, Hf, Nb, Mg, Al, Sr, Y, Ba, Ca, As, Sb, Bi, Sn, Pb, Co, lanthanides (such as Er), or combinations thereof), the two-step process above may be followed by introduction of a second vapor of a metal-containing precursor into the reaction chamber. The metal-containing precursor will be selected based on the nature of the silicon metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the organosilane precursor, metal-containing precursor, and oxygen source, a film of desired composition and thickness can be deposited.

Additionally, by varying the number of pulses, films having a desired stoichiometric M:Si ratio may be obtained. For example, a SiMO$_2$ film may be obtained by having one pulse of the organosilane precursor and one pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

In another alternative, Si or dense SiCN films may be deposited via an ALD or modified ALD process using the disclosed compounds and a halosilane compound having the formula Si$_a$H$_{2a+2-b}$X$_b$, wherein X is F, Cl, Br, or I; a=1 through 6; and b=1 through (2a+2); or a cyclic halosilane compound having the formula —Si$_c$H$_{2c-d}$X$_d$—, wherein X is F, Cl, Br, or I; c=3-8; and d=1 through 2c. Preferably the halosilane compound is trichlorosilane, hexachlorodisilane (HCDS), pentachlorodisilane (PCDS), tetrachlorodisilane, or hexachlorocyclohexasilane. One of ordinary skill in the art will recognize that the Cl in these compounds may be substituted by Br or I when lower deposition temperatures are necessary, due to the lower bond energy in the Si—X bond (i.e., Si—Cl=456 kJ/mol; Si—Br=343 kJ/mol; Si—I=339 kJ/mol). If necessary, the deposition may further utilize an N-containing co-reactant, such as NH$_3$. Vapors of the disclosed precursors and the halosilane compounds may be introduced sequentially or simultaneously into the reactor, depending on the desired concentration of the final film. The selected sequence of precursor injection will be determined based upon the desired film composition targeted. The precursor introduction steps may be repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the NH$_3$ co-reactant in order to tune the amounts of carbon and nitrogen in the SiCN film.

In yet another alternative, a silicon-containing film may be deposited by the flowable PECVD method disclosed in U.S. Pat. App. Pub. No. 2014/0051264 using the disclosed compounds and a radical nitrogen- or oxygen-containing co-reactant. The radical nitrogen- or oxygen-containing co-reactant, such as NH$_3$ or H$_2$O respectively, is generated in a remote plasma system. The radical co-reactant and the vapor phase of the disclosed precursors are introduced into the reaction chamber where they react and deposit the initially flowable film on the substrate. Applicants believe that the nitrogen atoms of the amidinate groups in the disclosed compounds help to further improve the flowability of the deposited film, resulting in films having less voids.

The silicon-containing films resulting from the processes discussed above may include Si, $SiO_2$, SiN, SiON, SiCN, SiCOH, or $MSiO_x$, wherein M is an element such as Hf, Zr, Ti, Nb, Ta, or Ge, and x may be 4, depending of course on the oxidation state of M. One of ordinary skill in the art will recognize that by judicial selection of the appropriate organosilane precursor and co-reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 600° C. for less than 3600 seconds under a H-containing atmosphere. The resulting film may contain fewer impurities and therefore may have improved performance characteristics. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the silicon-containing film.

EXAMPLES

The following non-limiting examples are provided to further illustrate embodiments of the invention. However, the examples are not intended to be all inclusive and are not intended to limit the scope of the inventions described herein.

Example 1—Synthesis of $SiH_2(N^iPr\text{-}amd)_2$

Under an atmosphere of dry $N_2$, a 3-necked flask (equipped with a −78° C. condensor) was chilled to −78° C. Anhydrous diethyl ether (100 mL) was added and then dichlorosilane was added (17.2 g, 0.170 mol) at a rate of 60 sccm. A freshly prepared 0° C. suspension of lithium amidinate (0.342 mol) in diethyl ether (314 mL) was transferred into the reaction flask. After the addition (and due to other time constraints), the resulting colorless suspension was stirred overnight at −78° C. As shown in FIG. 1, gas chromatography analysis of the colorless suspension revealed a mixture of the target product and diethyl ether with no other detectable impurities. Further testing is ongoing to determine the best method to isolate the product from the crude mixture.

Example 2—Synthesis of $SiH_2(N^iPr\text{-}amd)_2$

Under an atmosphere of dry $N_2$, a 3-necked flask (equipped with a −78° C. condensor and dropping funnel) was loaded with silicon tetrachloride (14.8 mL, 0.129 mol) and anhydrous diethyl ether (100 mL), then cooled in a dry ice bath to −40° C. A freshly prepared 0° C. suspension of lithium amidinate (0.259 mol) in diethyl ether (260 mL) was transferred into the reaction flask. After the lithium amidinate addition, the resulting colorless suspension was allowed to warm to room temperature with stirring for three hours. The reaction mixture was then cooled to −40° C. and a 2M solution of lithium aluminum hydride in THF (132 mL, 0.264 mol) was added. After the lithium aluminium hydride addition, the reaction was allowed to warm to room temperature and stirred for 3 hours. The suspension was filtered over a medium glass frit with a pad of Celite to obtain a cloudy, pale yellow liquid.

The following day, solvent and high volatiles were removed under reduced pressure to obtain a viscous yellow oil, which was distilled over a short path column (110-130° C., 300 mTorr) to obtain a colorless liquid which slowly crystallizes upon standing overnight. GCMS and 1H NMR show the product to be $SiCl_2(amd)_2$ (28 g, 57%). A trace amount (~1% area) of the desired product $SiH_2(amd)_2$ is also observed.

Example 3

Figure 2:
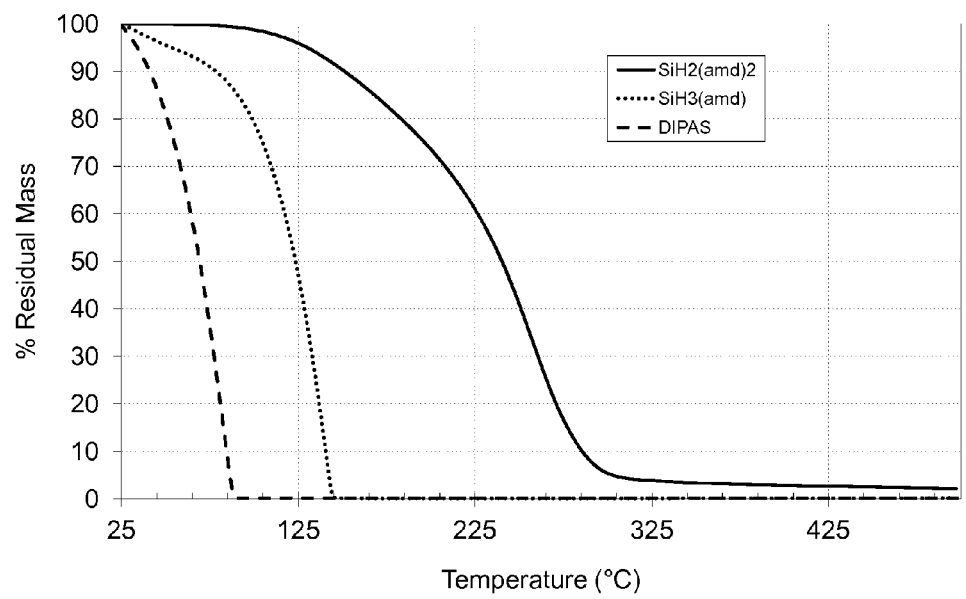
FIG. 2 is a thermogravimetric analysis (TGA) graph demonstrating the percentage of weight loss with temperature change for $SiH_2(N^iPr\text{-amd})_2$ as compared to that of DiPAS [$SiH_3(NiPr_2)$] and $SiH_3(N^iPr\text{-amd})$.

Thermogravimetric analysis was conducted on $SiH_2(N^{iPr}\text{-}amd)_2$, $SiH_3(N^{iPr}\text{-}amd)$, and $SiH_3(NHiPr)$. The temperature ramped from 25° C. to 500° C. at a rate of 10° C./minute under open cup atmospheric pressure conditions. The results shown in FIG. 2 show the good volatility and low residue of $SiH_2(N^{iPr}\text{-}amd)_2$, which suggests this compound will have favourable behaviour under vapour deposition process conditions.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A hexacoordinate silicon-containing molecule having the following formula:

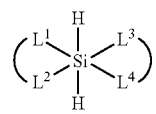

wherein each $L^1$, $L^2$, $L^3$ and $L^4$ is a nitrogen atom;

$L^1$ and $L^2$ are joined together via a carbon bridge having one to three carbon atoms;

$L^3$ and $L^4$ are joined together via a carbon bridge having one to three carbon atoms;

$L^1$, $L^2$ and the carbon bridge forming a monoanionic ligand bonded to silicon; and $L^3$, $L^4$ and the carbon bridge form a monoanionic ligand bonded to silicon.

2. The hexacoordinate silicon-containing molecule of claim 1, wherein the molecule has the following formula:

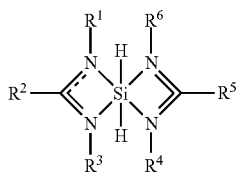

wherein R¹, R², R³, R⁴, R⁵ and R⁶ is each independently H, a C1 to C6 alkyl group, or a C3-C20 aryl or heterocycle group.

3. The hexacoordinate silicon-containing molecule of claim 1, wherein the molecule has the following formula:

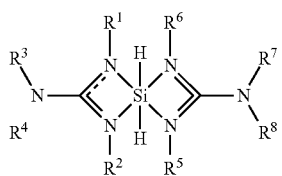

wherein R¹, R², R³, R⁴, R⁵, R⁶, R⁷ and R⁸ is each independently H, a C1 to C6 alkyl group, or a C3-C20 aryl or heterocycle group.

4. The hexacoordinate silicon-containing molecule of claim 1, wherein the molecule has the following formula:

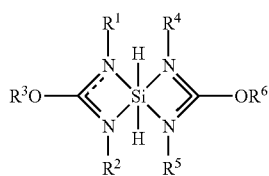

wherein R¹, R², R³, R⁴, R⁵, and R⁶ is each independently H, a C1 to C6 alkyl group, or a C3-C20 aryl or heterocycle group.

5. The hexacoordinate silicon-containing molecule of claim 1, wherein the molecule has the following formula:

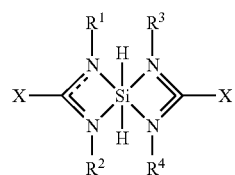

wherein R¹, R², R³, and R⁴ is each independently H, a C1 to C6 alkyl group, or a C3-C20 aryl or heterocycle group, and each X is independently Cl, Br, I, or F.

6. The hexacoordinate silicon-containing molecule of claim 1, wherein the molecule has the following formula:

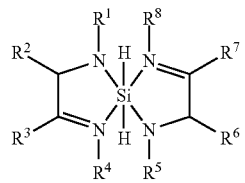

wherein R¹, R², R³, R⁴, R⁵, R⁶, R⁷ and R⁸ is each independently H, a C1 to C6 alkyl group, or a C3-C20 aryl or heterocycle group.

7. The hexacoordinate silicon-containing molecule of claim 1, wherein the molecule has the following formula:

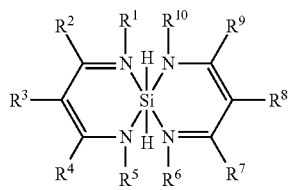

wherein R¹, R², R³, R⁴, R⁵, R⁶, R⁷, R⁸, R⁹, and R¹⁰ is each independently H, a C1 to C6 alkyl group, or a C3-C20 aryl or heterocycle group.

8. A method of deposition a Si-containing layer on a substrate, the method comprising:
introducing a vapor of the hexacoordinate silicon-containing molecule of claim 1 into a reactor having a substrate disposed therein; and
depositing at least part of the organosilane precursor onto the substrate to form a Si-containing layer using a vapor deposition method.

9. The method of claim 8, further comprising introducing a co-reactant into the reactor.

10. The method of claim 8, wherein the vapor deposition process is a chemical vapor deposition process.

11. The method of claim 8, wherein the vapor deposition process is an atomic layer deposition (ALD) process.

12. The method of claim 8, wherein the hexacoordinate silicon-containing molecule has the following formula:

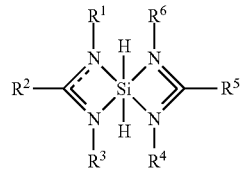

wherein R¹, R², R³, R⁴, R⁵ and R⁶ is each independently H, a C1 to C6 alkyl group, or a C3-C20 aryl or heterocycle group.

13. The method of claim 8, wherein the hexacoordinate silicon-containing molecule is SiH₂(N$^{iPr}$-amd)₂.

14. The hexacoordinate silicon-containing molecule of claim 2, wherein the hexacoordinate silicon-containing molecule is SiH₂(N$^{iPr}$-amd)₂.

* * * * *